United States Patent [19]

Umezawa et al.

[11] 4,207,313

[45] Jun. 10, 1980

[54] ANTHRACYCLINE ANTIBIOTICS

[75] Inventors: Hamao Umezawa; Tomio Takeuchi, both of Tokyo; Toshikazu Oki, Yokohama; Taiji Inui, Chigasaki, all of Japan

[73] Assignee: Zaidan Hojin Biseibutsu Kagaku Kenkyu Kai, Tokyo, Japan

[21] Appl. No.: 838,617

[22] Filed: Oct. 3, 1977

[30] Foreign Application Priority Data

Oct. 5, 1976 [JP] Japan ............................... 51-120237
May 24, 1977 [JP] Japan ............................... 52-60908

[51] Int. Cl.$^2$ ..................... A61K 31/71; C07H 15/24
[52] U.S. Cl. ............................ 424/181; 424/180; 536/17 R; 536/17 A; 536/28; 536/29; 435/78; 435/886
[58] Field of Search ............... 536/17, 17 A, 4, 28, 536/29; 424/180, 181

[56] References Cited

U.S. PATENT DOCUMENTS

| | | | |
|---|---|---|---|
| 3,828,021 | 8/1974 | Beattie et al. | 536/17 |
| 3,988,315 | 10/1976 | Umezawa et al. | 536/17 A |
| 4,009,328 | 2/1977 | Mallams et al. | 536/17 |
| 4,039,736 | 8/1977 | Nettleton, Jr. et al. | 536/17 A |
| 4,093,797 | 6/1978 | Oda et al. | 536/17 |

OTHER PUBLICATIONS

Nettleton, Jr. et al., "The Jour. of Antibiotics", vol. XXX, No. 6, pp. 525–529, 1977.

*Primary Examiner*—Johnnie R. Brown
*Attorney, Agent, or Firm*—David M. Morse

[57] ABSTRACT

New anthracycline glycosides designated MA 144-G1, -G2, -L, -S1, -N1, -U1 and -Y which inhibit the growth of gram-positive bacteria and experimental animal tumors are produced by fermentation of certain species of Streptomyces and by the chemical or enzymatic conversion of certain anthracycline glycosides. New microbiological and chemical processes are also provided for preparation of the anthracycline glycosides MA 144-S2 and -U2 which have been found to be identical with the previously reported anthracyclines, marcellomycin and musettamycin.

9 Claims, No Drawings

ANTHRACYCLINE ANTIBIOTICS

BACKGROUND OF THE INVENTION

1. Field of the Invention

This invention relates to new anthracycline antibiotics, to methods for their use as antimicrobial and antitumor agents, to pharmaceutical compositions containing them and to methods for the preparation and recovery of said new compounds as well as certain previously reported anthracycline antibiotics.

2. Description of the Prior Art

Various types of anthracycline glycosides have been found in the cultured broth of microorganisms and described in the literature. Among them, daunomycin and adriamycin have already been applied clinically for human cancers, and aclacinomycin A, carminomycin and rubidazone are under clinical trials with keen interest in the field of cancer chemotherapy.

As a result of screening cultures of Streptomyces for metabolites having antitumor activity, the present inventors have discovered new compounds and after purification and characterization based on their physico-chemical properties, they have confirmed that the antibiotics now named MA 144-G1, -G2, -L, N1, -S1, -U1 and -Y are new anthracycline glycosides which have potent antitumor activity and low toxicity in experimental animals. Additionally, they have established processes and methods for the preparation and purification of these new antibiotics as well as for the antibiotics named MA 144-S2 and -U2 which have been determined to be identical with the previously reported anthracycline glycosides, marcellomycin and musettamycin (see U.S. Pat. No. 4,039,736).

Preparation of adriamycin by fermentation of *S. peuceticus var. caseius* is disclosed in U.S. Pat. No. 3,590,028. Chemical conversion of daunomycin to adriamycin is taught in U.S. Pat. No. 3,803,124.

Daunomycin (produced by fermentation of *S. peuceticus* in U.K. Pat. No. 1,003,383) may be the same as Rhone-Poulenc's 13,057 R.P. (formerly rubidomycin and now daunoribicin; see U.K. Pat. Nos. 985,598, 1,188,262 and 1,241,750 and U.S. Pat. No. 3,616,242) and is probably identical to Ciba's danubomycin disclosed in U.S. Pat. No. 3,092,550 and U.K. Pat. No. 901,830. See also U.S. Pat. No. 3,686,163 on dihydrodaunomycin.

Anthracycline antibiotics having the aklavinone aglycone moiety are disclosed as follows:

(a) aclacinomycin A and B in U.S. Pat. No. 3,988,315 and by Oki et al. in J. Antibiotics 28:830 (1975).

(b) aklavin in J. Bacteriol. 72:90 (1956).

Anthracycline antibiotics having the ε-pyrromycinone aglycone moiety are described in the literature as follows:

(c) musettamycin and marcellomycin from bohemic acid complex in J. Antibiotics 30:525 (1977) and in U.S. Pat. No. 4,039,736.

(d) pyrromycin in Chem. Ber. 92:1904 (1959).

(e) cinerubin A and B in U.K. Pat. No. 846,130 (see also U.S. Pat. No. 3,864,480 and Keller-Schierlein et al. Antimicrobial Agents and Chemotherapy, page 68 (1970)).

Other anthracycline antibiotics having an aglycone different from aklavinone and ε-pyrromycinone are described in the following literature:

(f) nogalamycin in J. Amer. Chem. Soc. 99:542 (1977).

(g) steffimycin in J. Antibiotics 27:805, 809 (1974).

(h) carminomycin in J. Antibiotics 27:254 (1974), in U.K. Pat. No. 1,426,637 and in J. Amer. Chem. Soc. 97:5955 (1975).

(i) trypanomycin in Antimicrobial Agents and Chemotherapy 1:385 (1972).

(j) requinomycin in J. Antibiotics 25:393 (1972).

(k) galirubin A and B in Naturwiss. 52:539 (1965) and Chem. Abst. 67:90573z (1967).

For further illustrative and summary disclosures of anthracycline antibiotics, see Index of Antibiotics from Actinomycetes, Hamao Umezawa, Editor-in-Chief, University Park Press, State College, Pa., U.S.A. (1967) as follows:

| Antibiotic | Page Number |
| --- | --- |
| Aklavin | 111 |
| Cinerubin A | 220 |
| Cinerubin B | 221 |
| Danubomycin | 242 |
| Daunomycin | 243 |
| Pyrromycin | 524 |
| Rhodomycin A, B | 561 |
| Rubidomycin | 574 |

The textbook Antibiotics, Vol. 1, Mechanism of Action, edited by David Gottlieb and Paul D. Shaw, Springer-Verlag New York, Inc., N.Y., N.Y. (1967) at pages 190–210 contains a review by A. DiMarco entitled Daunomycin and Related Antibiotics. Information Bulletin, No. 10, International Center of Information of Antibiotics, in collaboratiion with WHO, December, 1972, Belgium, reviews kanthracyclines and their derivatives.

SUMMARY OF THE INVENTION

The present invention relates to anthracycline glycoside antibiotics named MA 144-G1, -G2, -L, -N1, -S1, -S2, -U1, -U2 and -Y. Compounds MA 144-G1, -G2, -L, -S1, -N1, -U1 and -Y are new antibiotics while compounds MA 144-S2 and -U2 are identical with the previously reported marcellomycin and musettamycin produced by fermentation of Actinosporangium sp. ATCC 31127 (see U.S. Patent 4,039,736). The antibiotics of the present invention may be produced either by fermentation of certain species of Streptomyces or by the chemical or enzymatic conversion of aclacinomycin A, cinerubin A, rhodirubin A, MA 144-M1, MA 144-M2, MA 144-G1, MA 144-G2, MA 144-U1, MA 144-U2, MA 144-Y or MA 144-N1, all of such processes being included in the present invention. The so-produced antibiotics may be recovered, separated and purified by conventional methods used to isolate and purify water-insoluble antibiotics, said methods including at least one process selected from the group consisting of solvent extraction, solvent precipitation, concentration, gel filtration, counter current distribution, chelation with metal ions and adsorption followed by elution from an ion exchange resin, adsorbent siliceous earth material or synthetic adsorbent.

This invention also embraces MA 144-G1, -G2, -L, -N1, -S1, -U1 and -Y as crude solids, as purified solids, as their non-toxic acid addition salts with organic and inorganic acids and as complexes with deoxyribonucleic acid. Also included are processes wherein a solution containing one of the above-mentioned novel antibiotics is lyophilized alone or with at least one substance selected from deoxyribonucleic acid, glycerol, sugars, amino acids, serum, serum albumin, globulin, gelatin and organic or inorganic acids.

DETAILED DESCRIPTION

The present invention provides the antitumor antibiotics MA 144-G1, -G2, -L, -N1, -S1, -S2, -U1, -U2 and -Y which have been found to (a) have antimicrobial activity against gram-positive bacteria, (b) be effective in inhibiting the growth of malignant tumors in experimental animals such as L1210 and P388 leukemia in mice, (c) have a high cytotoxicity and thus inhibit the growth and RNA synthesis of mammalian tumor cells in culture and (d) possess low toxicity. Accordingly the compounds are useful as antibacterial and antitumor agents.

The compounds MA 144-G1, -G2, -L, -N1, -S1, -U1 and -Y have been determined to be novel anthracycline glycosides. Subsequent to the filing date of the Japanese priority application (Showa 51-120237), the compounds MA 144-S2 and -U2 provided by the present invention were determined to be identical with the antibiotics marcellomycin and musettamycin disclosed in U.S. Pat. No. 4,039,736.

As used herein the term MA 144 refers to the antibiotic which includes at least one antibiotic selected from MA 144-G1, -G2, -L, -S1, -S2, -N1, -U1, -U2, and -Y.

The compounds provided by the present invention have been determined to have the following structures:

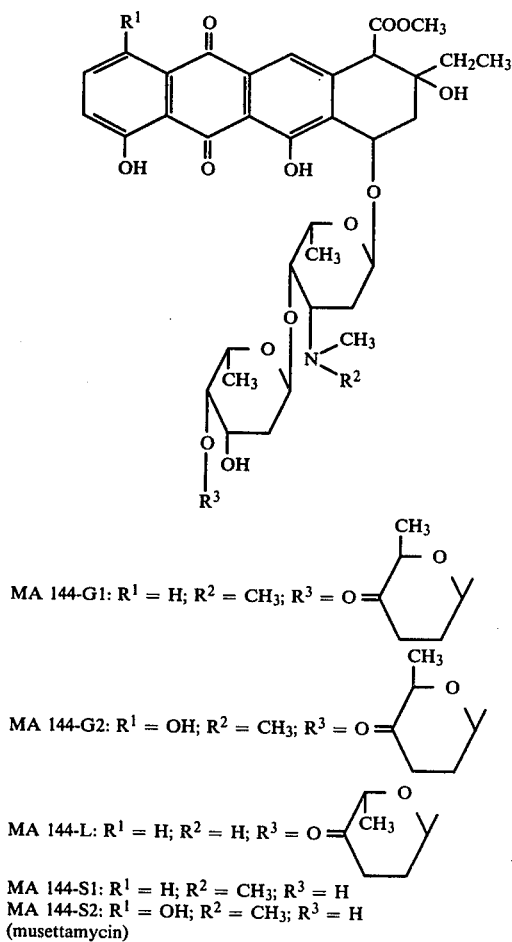

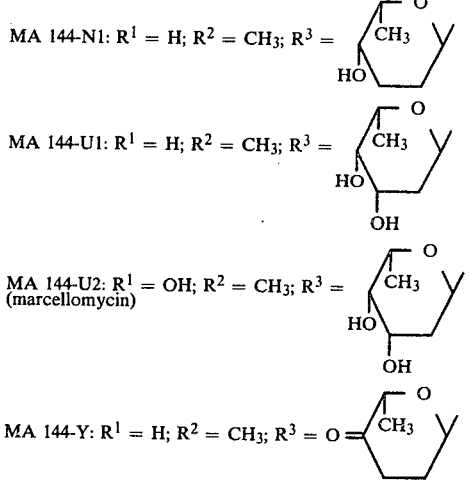

Production of MA 144 Antibiotics

The compounds of the present invention may be prepared by fermentation of MA 144-producing strains of Streptomyces. Some of the compounds can also be produced by chemical and enzymatic methods as described below.

For fermentative production of the MA 144 antibiotics of the present invention, MA 144-producing strains belonging to the genus Streptomyces can be used such as *Streptomyces galilaeus* MA 144-M1 (FERM P-2455, ATCC 31133), *Streptomyces galilaeus* (ATCC 14969), *Streptomyces cinereoruber* (ATCC 19740), *Streptomyces niveoruber* (ATCC 14971), *Streptomyces antibioticus* (ATCC 8663), *Streptomyces purpurascens* (ATCC 25489), Streptomyces sp. ME 505-HE1 (ATCC 31273) and mutants thereof. Since the Streptomyces are easily mutatable naturally or artificially, the present invention encompasses the particular strains described above and all natural and artificial MA 144-producing variants and mutants thereof.

Production of the MA 144 compounds is carried out by cultivating the appropriate strain of Streptomyces as indicated above in a conventional aqueous nutrient medium containing known nutritional sources for actinomycetes, i.e. assimilable sources of carbon, nitrogen and inorganic salts. Submerged aerobic culture is preferably employed for the production of substantial amounts of the MA 144 components, just as for other fermentation antibiotics. The general procedures used for the cultivation of other actinomycetes are applicable to the cultivation according to this invention. The medium preferably contains commercially available sources of assimilable carbon such as glucose, glycerol, starch, dextrin, sucrose, maltose, oils, fats and the like in either purified or crude state and commercially available sources of assimilable nitrogen such as soybean powder, yeast extract, peptone, cotton seed powder, dried yeast, corn steep liquor or inorganic salts such as ammonium sulfate, sodium nitrate or ammonium chloride. Inorganic salts such as chlorides (KCl, NaCl), phosphates, sulfates or carbonates are preferably used and there may also be added, if necessary, salts of trace metals such as iron, copper, magnesium, zinc, cobalt or manganese and defoamers such as liquid paraffin, soybean oil, fat or silicone. The fermentation temperature should be in the range of 20° to 37° C., preferably about 25°-30° C. The pH of the medium should be maintained in the range of about 6 to 9. Production of MA 144 components in the culture broth reaches a maximum after 2 to 7 days in either shake flask or submerged aerobic fermentation with aeration and agitatiin provided as in the illustrative examples below. The yield in the cultured broth can be monitored by chromatoscanner after developing on silica gel (thin layer chromatography) or by bioassay with *Bacillus subtilis*.

Certain of the MA 144 antibiotics may also be prepared by chemical or enzymatic processes.

According to one non-fermentation process, MA 144-S1 may be produced by acid hydrolysis of aclacinomycin A, MA 144-N1, MA 144-G1, MA 144-U1, MA 144-Y or MA 144-M1 while MA 144-S2 may be prepared by acid hydrolysis of rhodirubin A, cinerubin A, MA 144-G2, MA 144-U2 or MA 144-M2. The appropriate starting material anthracycline is treated with a mineral acid under mild conditions, e.g. room temperature for ~15 minutes, until the terminal sugar moiety is hydrolyzed off to give the desired endproduct. Following hydrolysis, the reaction mixture may be neutralized and the anthracycline product recovered as described below. Any mineral acid (preferably used in the form of a dilute aqueous solution) may be employed in the hydrolysis, e.g HCl, $H_2SO_4$ or $H_3PO_4$. The reaction may be readily seen from the following reaction scheme:

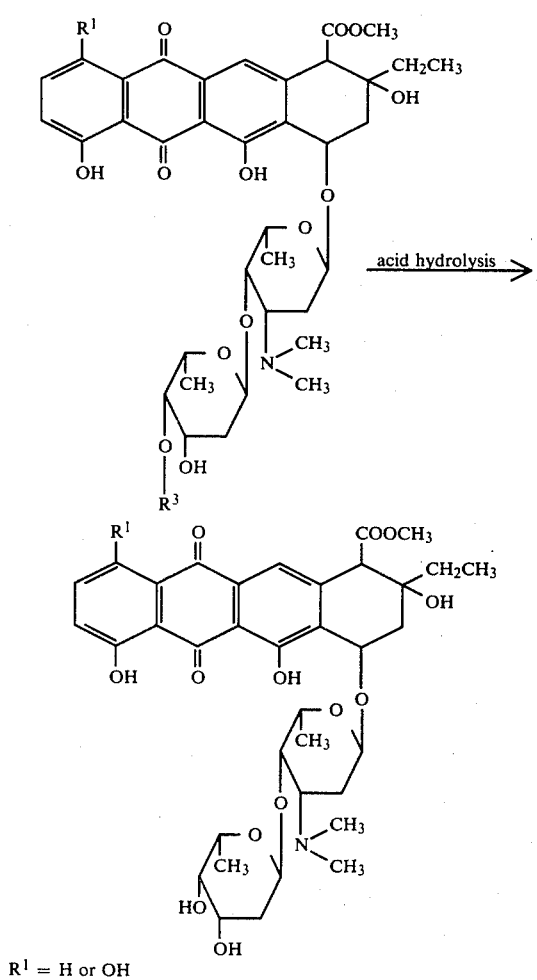

$R^1$ = H or OH

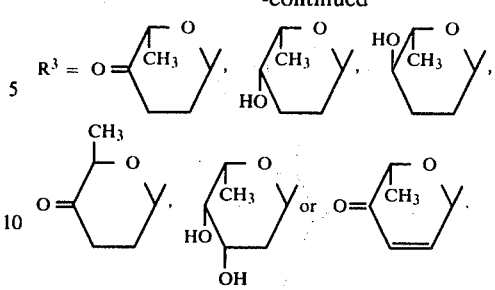

The starting material anthracyclines used in the hydrolysis reaction are either described in the literature or methods for their preparation are provided in the present application. Thus, aclacinomycin A is disclosed in U.S. Pat. No. 3,988,315. MA 144-N1, MA 144-G1, MA 144-U1, MA 144-Y, MA 144-G2 or MA 144-U2 may be prepared by the fermentation process described above. MA 144-M1 and -M2 are disclosed in U.S. application Ser. No. 780,730 filed Mar. 23, 1977, the entire disclosure of which is incorporated herein by reference; see also Part I of "Preparation of Starting Materials" in the present application. Cinerubin A is disclosed in U.K. Pat. No. 846,130. The structures of the various starting materials may be represented as follows:

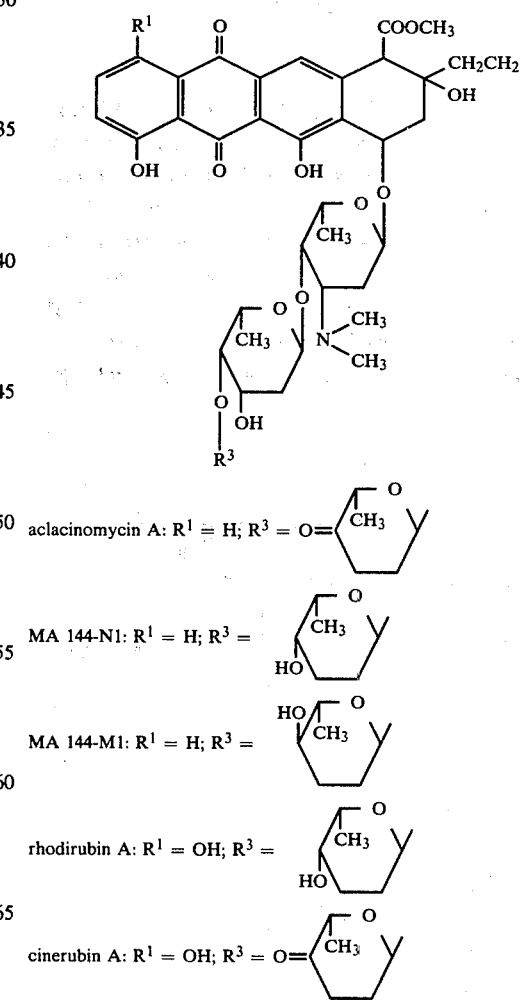

MA 144-M2: R¹ = OH; R³ = 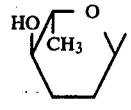

MA 144-G1: R¹ = H; R³ = O= 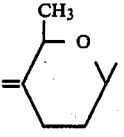

MA 144-G2: R¹ = OH; R³ = O= 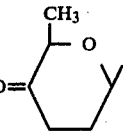

MA 144-U1: R¹ = H; R³ = 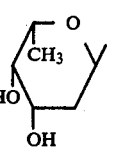

MA 144-U2: R¹ = OH; R³ = 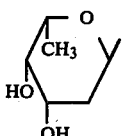

MA 144-Y: R¹ = H; R³ = O= 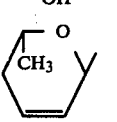

The starting materials may be used in purified form, in impure form, e.g. in the form of materials containing the anthracycline substances such as fermentation broths or crude extracts from such broths, or as salts.

Compound MA 144-N1 may also be prepared by selective reduction of the L-cinerulose A sugar moiety of aclacinomycin A to the L-rhodinose sugar of MA 144-N1 with either chemical reducing agents or by enzymatic reduction. The reaction scheme may be illustrated as follows:

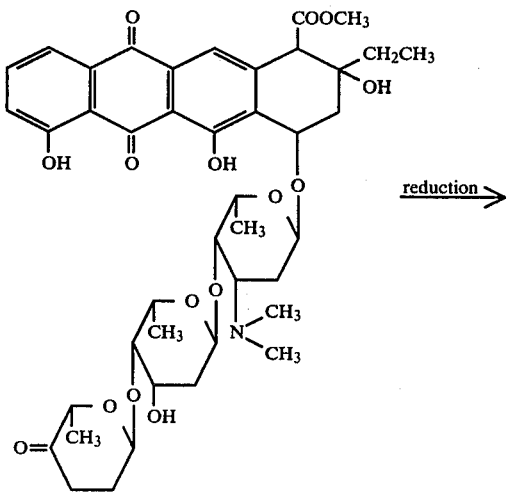 reduction⟶ 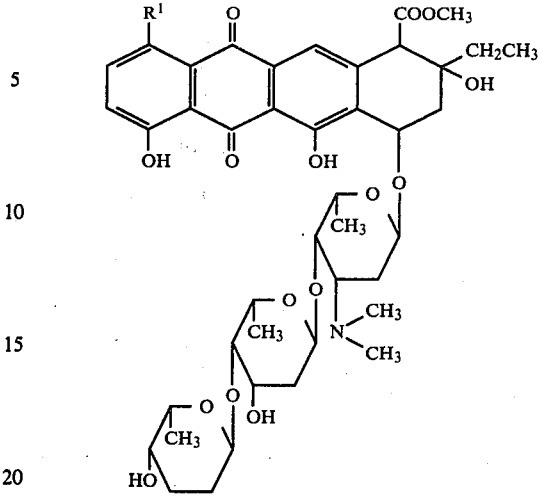

The chemical reduction may be carried out with reducing agents capable of selectively reducing a keto functional group in a sugar moiety to a hydroxyl group. Preferred reducing agents include hydrides such as $NaBH_4$, $LiH$, $LiAlH_4$, $AlH_3$, $AlH(C_4H_9)_2$, $NaAlH_2(OCH_2CH_2OCH_3)_2$, lithium tri-sec-butyl borohydride, potassium tri-sec-butyl borohydride or $BH_3.THF$. A most preferred reducing agent is $NaBH_4$. The reduction reaction may be carried out either in a single solvent system or a mixed solvent system. Reaction conditions such as temperature, substrate concentration, reaction period, etc. may be optimized by simple test and are dependent on various factors such as the particular reducing agent and solvent selected. The aclacinomycin A starting material may be employed in either pure or impure form or as a salt.

In the enzymatic reduction procedure, aclacinomycin A (in pure or impure form or as a salt) is incubated in a medium containing an enzyme capable of selectively reducing the L-cinerulose A sugar moiety to the L-rhodinose sugar of MA 144-N1 and a coenzyme, said enzyme system being obtained from mammalian tissue (e.g. tissues from monkeys, dogs, rabbits, hamsters, guinea pigs, rats or mice) or from microorganisms belonging to the genus Streptomyces and said coenzyme being NADPH or NADH. In the case of the microorganism-derived enzyme, the reductase enzyme occurs widely in the microsome fraction of Streptomyces strains. Specific strains which may be used include the seven MA 144-producing strains of Streptomyces mentioned above in connection with the fermentation process. In employing the microorganism-derived enzyme system, there may be used the cultured broth of the microorganism, cell suspension obtained therefrom, dried cells obtained therefrom, cell homogenate obtained therefrom, microsome fraction obtained therefrom, partially purified enzyme obtained therefrom or immobilized enzyme obtained therefrom. In the case of enzyme derived from mammalian tissue, various enzyme sources such as organs, tissue slices, tissue homogenates, their dried preparations, partially purified enzyme (obtained, for example, by salting out, organic solvent precipitation, gel filtration or adsorption chromatography) or immobilized enzyme may be used. The conditions of the enzyme reaction such as pH, temperature, substrate concentration, reaction period, coenzyme, etc. depend upon the state of the enzyme, form of starting material used, etc. Generally speaking, it is preferable to select the conditions which accelerate the enzyme reaction and which do not inactivate the enzyme system. In general, temperatures from 20° to 42° C., pH from 5.5 to 10.5 (optimal pH is 6 to 8), a substrate concentration under 5% and a reaction period from 20 to 120 min. under aerobic conditions are preferable. NADH and NADPH can be used as coenzymes. $Cu^{++}$, $Hg^{++}$, $Fe^{+++}$, PCMB and N-ethylmaleimide are inhibitors for the enzyme reaction. (PCMB=p-chloromercuribenzoic acid)

Antibiotic MA 144-Y may also be prepared by enzymatic conversion of aclacinomycin A or MA 144-N1 according to the following reaction scheme:

Antibiotic MA 144-Y may also be prepared by enzymatic conversion of aclacinomycin A or MA 144-N1 according to the following reaction scheme:

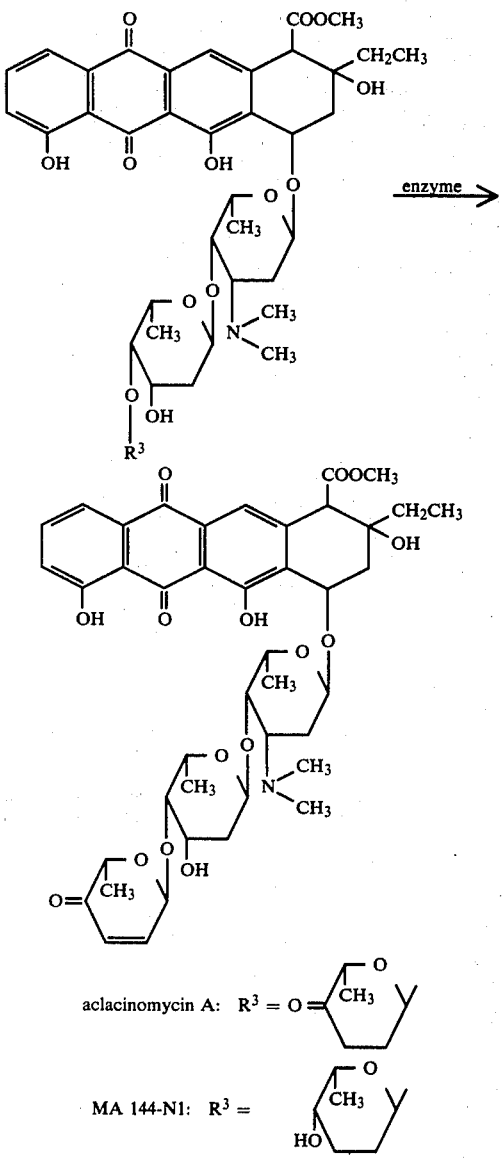

In this process aclacinomycin A or MA 144-N1 (in pure or impure form or as a salt) is incubated in a medium containing an enzyme system capable of converting the L-cinerulose A or L-rhodinose sugar moieties of aclacinomycin A or MA 144-N1 to the aculose sugar moiety of MA 144-Y. The converting enzyme is found in various Streptomyces strains which produce anthracycline glycosides having an aklavinone or ε-pyrromycinone aglycone. Specific Streptomyces strains which may be used include the seven MA 144-producing organisms discussed above in connection with the fermentation process. In employing the microbial enzyme system, there may be used the cultured broth, mycelia obtained therefrom, culture filtrate obtained therefrom, cell homogenate obtained therefrom, partially purified or purified enzyme obtained therefrom and immobilized enzyme obtained therefrom.

The conditions of the enzyme reaction such as pH, temperature, substrate concentration, reaction period, etc., depend upon the state of the enzyme, the form of starting material used, etc. Generally speaking, it is preferable to select the conditions which accelerate and do not inhibit the enzyme reaction. Preferred conditions include a temperature from about 20°–50° C., pH from about 4.0 to 9.0, a substrate concentration under 5% and a reaction period of from 10 minutes to 5 hours depending on the amount of dissolved oxygen present. The enzyme system requires oxygen but not coenzyme. While sufficient oxygen is generally available from the amount dissolved in the reaction mixture, oxygen gas may be advantageously aerated into the reaction mixture.

The enzyme activity in various Streptomyces used in the present invention are shown as follows:

Comparison of Enzyme Activity of Various Streptomyces

| Organisms | Enzyme activity (units/ml.) |
|---|---|
| Streptomyces galilaeus MA 144-M1 (ATCC 31133) | 100 |
| St. galilaeus ATCC 14969 | 75 |
| St. sp. ME 505-HE1, ATCC 31273 | 25 |
| St. cinereoruber ATCC 19740 | 85 |
| St. niveoruber ATCC 14971 | 35 |
| St. antibioticus ATCC 8663 | 15 |
| St. purpurascens ATCC 25489 | 20 |

Composition of the enzyme reaction mixture of 1 ml.

| | |
|---|---|
| Aclacinomycin A as substrate (0.4 μmole/ml.) | 0.25 ml. |
| 0.2 M citrate buffer (pH 5.5) | 0.25 ml. |
| Enzyme solution | 0.50 ml. |

The reaction was carried out for 30 min. at 37° C. followed by termination in an ice bath and addition of 1 ml. of 0.2 M Tris-HCl buffer (pH 7.5). The reaction products were extracted with 0.25 ml. of toluene, developed on silicic acid thin-layer, and determined by using a Shimazu Dual-wave chromatoscanner Model CS900. A unit of enzyme activity is defined as the amount of enzyme forming 0.001 μmole of MA 144-Y per min.

For the purification of the converting enzyme from the seven strains of Streptomyces described above, conventional methods of enzyme purification can be employed. For example, the purified enzyme preparation homogeneous electrophoretically can be obtained from the culture filtrate by precipitation from a 50% saturated solution of ammonium sulfate and chromatography on DEAE-cellulose, DEAE-Sephadex A-50 and Sephadex G-75. General properties of the purified enzyme obtained from *Streptomyces galilaeus* MA 144-M1 (ATCC 31133) are as follows:

| | |
|---|---|
| Molecular weight | 72,000 |
| Isoelectric point | pH 5.9 |
| Optimal pH | 5.5 |
| pH stability | 5.0 to 8.0 |
| Thermal stability | under 50° C. (neutral pH) |
| Reaction condition | Oxygen dependent |
| Km | 0.125 mM |
| Inhibitors | $Fe^{++}$, $SO_3^{--}$, $S_2O_4^{--}$, $S_2O_5^{--}$, $NaN_3$, Ascorbic acid, NADPH and hydrogen donors |

The properties of the enzymes obtained from all seven strains of Streptomyces mentioned above are identical with those from *Streptomyces galilaeus* MA 144-M1.

Separation and Isolation of MA 144 Components

The compounds in the present invention can be recovered from the cultured broth or from the chemical or enzymatic reaction mixtures and separated from each other by the following procedures.

MA 144 components produced by fermentation exist intracellularly as well as extracellularly, but are mainly found in the mycelium. To recover MA 144 components from the cultured broth, the broth may be filtered and the filtrate then extracted with a water-immiscible organic solvent such as chloroform, ethyl acetate, toluene, benzene, butyl acetate, n-butanol, methyl propyl ketone, methylene chloride etc., in a neutral or weakly acidic state. MA 144 components in the mycelium can be recovered by extraction with an organic solvent such as chloroform, acetone, n-butanol, methanol, ethanol, ethyl acetate or an aqueous solution of an organic or inorganic acid such as hydrochloric acid or acetic acid. Alternatively, MA 144 components can be extracted directly from the cultured broth by the above-mentioned extraction procedures without prior separation of the mycelium. After concentrating in vacuo, the MA 144 extracts may be re-extracted with a water-immiscible organic solvent at a pH between 6 and 9 and, after concentration under reduced pressure, the MA 144 concentrates are mixed with acidic aqueous solution having a pH less than 4. MA 144 components in said acidic aqueous solution are re-extracted with an organic solvent after adjustment to a weakly basic pH. By repeating the above procedures, if necessary, MA 144 components can be prepared in a purified form. As an alternative to using a solvent extraction recovery method or in combination with such a method, MA 144 components may be recovered from the cultured broth by column chromatography using adsorbents such as activated carbon, alumina, silicic acid, or a modified dextran such as that commercially available under the trade name Sephadex LH-20 (Pharmacia Fine Chem. Co., New York), countercurrent distribution or liquid chromatography using suitable organic solvents. Active extracts obtained by such methods are concentrated under reduced pressure and obtained as the red or yellow powders of the MA 144 components.

MA 144 components in the chemical and enzymatic reaction mixtures are extracted after addition of water, purified and obtained as a crude powder according to the above-mentioned recovery procedures. The solution containing the MA 144 components can also be lyophilized alone or with at least one substance selected from serum, serum albumin, globulin, gelatin, glycerol, sugars, amino acids, deoxyribonucleic acid and organic or inorganic acids such as hydrochloric acid, phosphoric acid, sulfuric acid, acetic acid, propionic acid, oleic acid, palmitic acid, citric acid, succinic acid and pantothenic acid.

To obtain the individual MA 144 components MA 144-G1, -G2, -L, -N1, -S1, -S2, -U1, -U2 and -Y, further purification and separation may be carried out using such standard separation techniques as column chromatography using various adsorbents such as silicic acid, modified dextrans, weakly acidic ion-exchange resins or activated carbon, counter current distribution, liquid chromatography using suitable organic solvents, or chelation with various metal ions, or a combination of one or more of the above-mentioned processes.

Physicochemical Properties of MA 144 Components

The physicochemical properties of MA 144-G1, G2, -L, -N1, -S1, -S2, -U1, -U2 and -Y are as follows:

| MA 144 | G1 | G2 |
|---|---|---|
| Appearance | Weak basic amorphous yellow powder | Weak basis amorphous red powder |
| Elementary analysis | C   H   N   O | C   H   N   O |
| Found | 61.45  6.31  1.44  28.93 | 61.15  6.21  1.75  30.58 |
| Calcd. | 62.14  6.58  1.73  29.56 | 60.93  6.45  1.69  30.92 |
| Empirical formula | $C_{42}H_{53}O_{15}N$ | $C_{42}H_{53}O_{16}N$ |
| Molecular weight | 811.9 | 827.9 |
| Melting point (°C.) | 141–145 | 152–156 |
| Specific rotation $[\alpha]_D^{20}$ | +54 (c = 0.33, $CHCl_3$) | |
| Solubility | Soluble in acidic water, methanol, ethanol, n-butanol, acetone, ethyl acetate, chloroform, benzene, toluene, dimethylsulfoxide, methyl cellosolve, dimethylformamide. Slightly soluble in water, n-hexane, cyclohexane, diethyl ether and petroleum. The hydrochloride salt is soluble in water, methanol, ethanol, but slightly soluble in chloroform, acetone and ethyl acetate. | |
| $R_f$ values** *C:M = 20:1 (v/v) | 0.38 | 0.38 |
| Reaction | Acidic aqueous and methanol solution is yellow and turns to reddish purple in alkaline state, and turns to reddish brown in conc. $H_2SO_4$ solution. | Acidic aqueous solution is red and turns to purplish blue in alkaline state, and turns to purple in conc. $H_2SO_4$ solution. |
| UV and visible absorption spectra and max $(E_{cm}^{1\%})$ in MeOH | 230 (537), 259 (330), 290 (140), 432 (165) | 235 (580), 259 (295), 292 (101), 492 (175) |
| in 0.1 N HCl— MeOH | 229.5 (610), 259 (372), 289 (159), 430 (169) | 235 (627), 259 (300), 292 (104), 492 (178) |
| in 0.1N NaOH— MeOH | 239 (521), 285 (151), 317 (96), 522 (144) | 242 (575), 565 (230), 605 (198) |
| Infrared absorption spectrum (KBr) principal bands | 3450, 2900, 1730, 1680, 1620, 1300, 1010 | 3450, 2900, 1740, 1600, 1450, 1300, 1220, 1010 |

| MA 144 | G1 | G2 |
|---|---|---|
| in $cm^{-1}$ | | |
| NMR spectrum (PMR in $CDCl_3$) ***chemical shifts in ppm δ | 7.2–7.9, m; 5.6, m; 5.3, m; 5.0, m; 3.7, s; 2.2 s; 1.0–1.5, m | 7.7, s; 7.2, s; 5.6, m; 5.3, m; 5.0, m; 3.7, s; 2.2, s; 1.0–1.5, m |

*C = chloroform, M = methanol
**TLC condition: Silicic acid thin-layer $60F_{254}$ (Merck Co.)
***multiplicity abbreviations: s = singlet m = multiplet d = doublet

| MA 144 | L | N1 |
|---|---|---|
| Appearance | Weak basic amorphous yellow powder | Weak basis amorphous red powder |
| Elementary analysis | C H N O | C H N O |
| Found | 61.39 6.31 1.54 30.13 | 61.43 6.71 1.71 29.22 |
| Calcd. | 61.72 6.44 1.76 30.08 | 61.97 6.82 1.72 29.48 |
| Empirical formula | $C_{41}H_{51}O_{15}N$ | $C_{42}H_{55}O_{15}N$ |
| Molecular weight | 797.9 | 813.9 |
| Melting point (°C.) | 134–136 | 146–147 |
| Specific rotation $[\alpha]_D^{20}$ | | +57.5 (C = 0.4, $CHCl_3$) |
| Solubility | Same as MA 144-Cl | Same as MA 144-G1 |
| $R_f$ values** *C:M = 20:1 (v/v) | 0.31 | 0.21 |
| Reaction | Same as MA 144-G1 | Same as MA 144-G1 |
| UV and visible absorption spectra and max ($E_{cm}^{1\%}$) in MeOH | 230 (480), 259 (298), 290 (118), 433 (151) | 229.5 (482), 259 (298) 290 (121), 433 (144) |
| in 0.1N HCl—MeOH | 230 (530), 259 (324), 290 (128), 433 (156) | 229.5 (488), 259 (304) 290 (123), 433 (151) |
| in 0.1N NaOH—MeOH | 238 (412), 287 (100), 318s (68), 525 (140) | 239 (450), 287 (121), 3185 (76), 525 (133) |
| Infrared absorption spectrum (KBr) principal bands in $cm^{-1}$ | 3450, 2900, 1730, 1680, 1620, 1300, 1010 | 3400, 2900, 1730, 1670, 1620, 1290, 1000 |
| NMR spectrum (PMR in $CDCl_3$) ***chemical shifts in pmm δ | 7.1–7.9, m; 5.6, m; 5.3, m; 5.0, m; 3.7, s; 2.3, s; 1.0–1.5, m; | 7.1–7.9, m; 5.6, m; 5.3, m; 5.2, m; 3.7, s 2.2, s; 1.0–1.5, m |

| MA 144 | S1 | S2 |
|---|---|---|
| Appearance | Weak basic amorphous yellow powder | Weak basic amorphous red powder |
| Elementary analysis | C H N O | C H N O |
| Found | 61.37 6.45 1.97 29.36 | 60.09 6.13 1.88 30.94 |
| Calcd. | 61.79 6.84 2.00 29.72 | 60.41 6.34 1.96 31.13 |
| Empirical formula | $C_{36}H_{45}O_{13}N$ | $C_{36}H_{45}O_{14}N$ |
| Molecular weight | 699.8 | 715.8 |
| Melting point (°C.) | 144–147 | 154–158 |
| Specific rotation $[\alpha]_D^{20}$ | +77° (c = 1.0, $CHCl_3$) | |
| Solubility | Same as MA 144-G1 | Same as MA 144-G1 |
| $R_f$ values** *C:M = 20:1 (v/v) | 0.14 | 0.14 |
| Reaction | Same as MA 144-G1 | Same as MA 144-G2 |
| UV and visible absorption spectra and max ($E_{cm}^{1\%}$) in MeOH | 230 (638), 258.5 (371), 289.5 (160), 432 (177) | 234.5 (607), 258.5 (306), 293 (110), 491 (189) |
| in 0.1N HCl—MeOH | 229.5 (652), 258.5 (380), 289.5 (163), 431 (192) | 234.5 (629), 258, (318), 293 (114), 491 (197) |
| in 0.1N NaOH—MeOH | 237.5 (553), 286 (141), 320 (90), 524 (161) | 242 (606), 566 (244), 606 (210) |
| Infrared absorption spectrum (KBr) principal bands in $cm^{-1}$ | 3450, 2950, 1730, 1670, 1620, 1300, 1010 | 3450, 2950, 1730, 1600, 1450, 1300, 1220, 1010 |
| NMR spectrum (PMR in $CDCl_3$) ***chemical shifts in ppm | 7.1–7.8, m; 5.6, m; 5.3, m; 5.0, m; 3.7, s; 2.2, s; 1.0–1.5, m | 7.7, s; 7.1, s; 5.6, m; 5.3, m; 5.0, m; 3.7, s; 2.2, s; 1.0–1.5, m |

| MA 144 | U1 | U2 |
|---|---|---|
| Appearance | Weak basic amorphous yellow powder | Weak basic amorphous red powder |
| Elementary analysis | C H N O | C H N O |
| Found | 60.42 6.77 1.74 31.07 | 59.26 6.60 1.58 31.87 |
| Calcd. | 60.79 6.68 1.69 30.85 | 59.64 6.55 1.65 32.15 |
| Empirical formula | $C_{42}H_{55}O_{16}N$ | $C_{42}H_{55}O_{17}N$ |
| Molecular weight | 829.9 | 845.9 |
| Melting point (°C.) | 152–155 | 160–164 |
| Specific rotation $[\alpha]_D^{20}$ | +31° (c = 1.0, $CHCl_3$) | |
| Solubility | Same as MA 144-G1 | Same as MA 144-G1 |
| $R_f$ values** *C:M = 20:1 (v/v) | 0.07 | 0.07 |
| Reaction | Same as MA 144-G1 | Same as MA 144-G2 |
| UV and visible absorption spectra and max ($E_{cm}^{1\%}$) in MeOH | 230 (531), 259 (325), 290 (135), 432 (164) | 235 (452), 259 (247), 292 (104), 492 (150) |
| in 0.1N HCl—MeOH | 229.5 (602), 259 (365), 289 (150), 430 (168) | 235 (465), 259 (250), 292 (103), 492 (152) |
| in 0.1N NaOH—MeOH | 239 (520), 285 (143), 317 (94), 522 (144) | 242 (448), 566 (200), 606 (164) |

| MA 144 | U1 | U2 |
|---|---|---|
| Infrared absorption spectrum (KBr) principal bands in cm$^{-1}$ | 3450, 2900, 1730, 1670, 1610, 1300, 1000 | 3450, 2950, 1730, 1600 1450, 1300, 1220, 1010 800 |
| NMR spectrum (PMR in CDCl$_3$) ***chemical shifts in ppm δ | 7.0–7.7, m; 5.6, m; 5.3, m; 5.0, m; 3.7, s; 2.1, s; 1.0–1.7, m | 7.7, s; 7.1, s; 5.6, m; 5.3, m; 5.1, m; 3.7, s; 2.2, s; 1.0–1.5, m |

| MA 144 | Y | | | |
|---|---|---|---|---|
| Appearance | Weak basic amorphous yellow powder | | | |
| Elementary analysis | C | H | N | O |
| Found | 61.98 | 6.30 | 1.70 | 30.02 |
| Calcd. | 62.29 | 6.35 | 1.73 | 29.63 |
| Empirical formula | C$_{42}$H$_{51}$O$_{15}$N | | | |
| Molecular weight | 810 | | | |
| Melting point (°C.) | 153–155 | | | |
| Specific rotation [α]$_D^{20}$ | +66 (c = 1.0, CHCl$_3$) | | | |
| Solubility | Same as MA 144-G1 | | | |
| R$_f$ values** | 0.47 | | | |
| *C:M = 20:1 (v/v) Reaction | Same as MA 144-G1 | | | |
| UV and visible absorption spectra and max ($E_{cm}^{1\%}$) in MeOH | 229.5 (580), 259 (320), 290 (126), 432 (158) | | | |
| in 0.1N HCl—MeOH | 229.5 (590), 259 (334), 290.5 (130), 433 (160) | | | |
| in 0.1N NaOH—MeOH | 239 (497), 287 (133), 320s (82), 524 (138) | | | |
| Infrared absorption spectrum (KBr) principal bands in cm$^{-1}$ | 3500, 2950, 1730, 1700, 1680, 1620, 1290, 1000 | | | |
| NMR spectrum (PMR in CDCl$_3$) ***chemical shifts in ppm δ | 7.0–7.8, m; 6.8, m; 6.1, d; 5.6, m; 5.3, m; 5.0, m; 3.7, s; 2.1, s; 1.0–1.7, m | | | |

Structure Determination

The structures of MA 144-G1, -G2, -L, -N1, -S1, -S2, -U1, -U2 and -Y in the present invention were determined as follows:

On acid hydrolysis with 0.1 N hydrochloric acid for 30 min. at 85° C., physicochemical properties, such as the absorption spectra in the ultraviolet, visible and infrared ranges, mass and nuclear magnetic resonance, melting point, elementary analysis and R$_f$ values on silicic acid thin-layer, of the aglycone portion obtained from MA 144-G1, -L, -N1, -S1, -U1 and -Y coincided fully with those of aklavinone (Tetrahedron Lett. No. 8, 28–34, 1960), and those of the aglycone portion obtained from MA 144-G2, -S2, and -U2 coincided fully with those of ε-pyrromycinone (Chem. Ber. 92, 1880–1903, 1959). On the other hand, the sugar moieties existing in the water soluble fraction of the above hydrolysates were determined by silicic acid thin-layer chromatography (Merck Co. 60F$_{254}$ silicic acid plate, n-butanol:acetic acid:water=4:1:1) after neutralization and concentration. The R$_f$ values of the sugars were compared with those of the authentic sugars obtained from aclacinomycin A (J. Antibiotics, 28, 830–834, 1975) and streptolydizin (J. Amer. Chem. Soc. 86, 3592–3594, 1972). R$_f$ values of the sugar moieties obtained from the MA 144 components are shown in the following table. There are three kinds of sugars in MA 144-G1, -G2, -L, -Y and -N1 and two kinds of sugars in MA 144-S1, -S2, -U1 and -U2.

| R$_f$ values of sugar moiety of MA 144 components | | | | | | |
|---|---|---|---|---|---|---|
| | R$_f$ value | | | | | |
| Compounds | 0.16 | 0.20 | 0.60 | 0.72 | 0.83 | 0.78 |
| MA 144-G1 | + | − | + | − | + | − |
| -G2 | + | − | + | − | + | − |
| -L | − | + | + | − | + | − |
| -N1 | + | − | + | + | − | − |
| -S1 | + | − | + | − | − | − |
| -S2 | + | − | + | − | − | − |
| -U1 | + | − | + | − | − | − |
| -U2 | + | − | + | − | − | − |
| -Y | + | − | + | − | − | + |

From the R$_f$ value comparisons, various color reactions and optical rotations of the authentic sugars, the sugar moiety corresponding to R$_f$=0.16 was identified as L-rhodosamine, R$_f$=0.60 was 2-deoxy-L-fucose, R$_f$=0.72 was L-rhodinose and R$_f$=0.83 was L-cinerulose. The sugars of R$_f$=0.20 and 0.78 have not been reported in the literature.

On partial methanolysis of the MA 144 components in methanol containing 0.01 N hydrochloric acid at room temperature, MA 144-G1, -N1, -S1, -U1 and -Y gave 1-deoxypyrromycin (L-rhodosaminyl alkavinone, J. Antibiotics, 28, 830–834, 1975), which was identified on the basis of its physicochemical properties such as R$_f$ value on silicic acid thin-layer, melting point, IR, UV and visible light absorption spectra and NMR spectrum and the corresponding methylated saccharides. MA 144-G2, -S2 and -U2 gave pyrromycin (Chem. Ber. 92, 1880–1903, 1959) and the corresponding methylated saccharides while MA 144-L gave an unknown anthracycline glycoside and the corresponding methylated disaccharide.

The following general formulae of MA 144-G1 [D-cinerulosyl-2-deoxy-L-fucosyl-L-rhodosaminyl-aklavinone] and MA 144-G2 [D-cinerulosyl-2-deoxy-L-fucosyl-L-rhodosaminyl-ε-pyrromycinone] were determined by NMR, $^{13}$C-NMR and IR spectra of said compounds and those of the methylated disaccharides thereof.

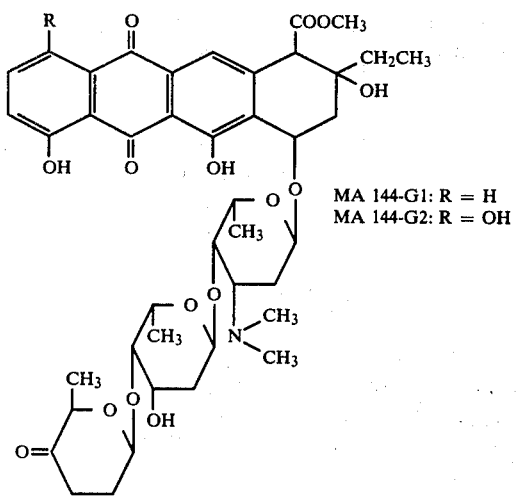

MA 144-G1: R = H
MA 144-G2: R = OH

MA 144-L consists of aklavinone and three sugar moieties: a previously unreported amino sugar having $R_f$ value of 0.20, 2-deoxy-L-fucose and L-cinerulose. Analysis of NMR and $^{13}$C-NMR spectra of the aklavinone-glycoside and the methylated disaccharide obtained from MA 144-L by methanolysis showed that they are N-monodemethyl-L-rhodosaminyl aklavinone and methyl cinerulosyl-2-deoxy-L-fucoside (found in aclacinomycin A), respectively.

Thus, the chemical structure of MA 144-L was determined to be as follows:

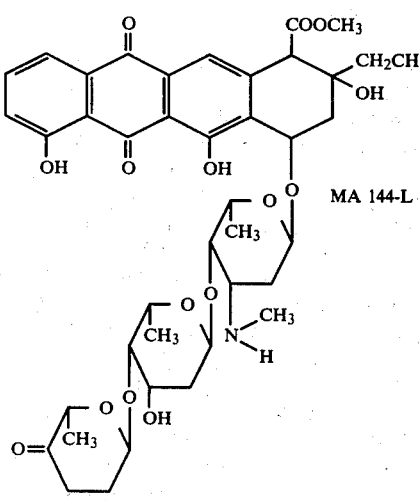

MA 144-L

MA 144-S1 and -S2 contain two kinds of sugar moieties, L-rhodosamine and 2-deoxy-L-fucose. Methyl 2-deoxy-L-fucoside and 1-deoxypyrromycin or pyrromycin were formed by methanolysis, and thus the following 2-deoxy-L-fucosyl-L-rhodosaminyl-aklavinone or -ε-pyrromycinone structures were demonstrated for MA 144-S1 and -S2.

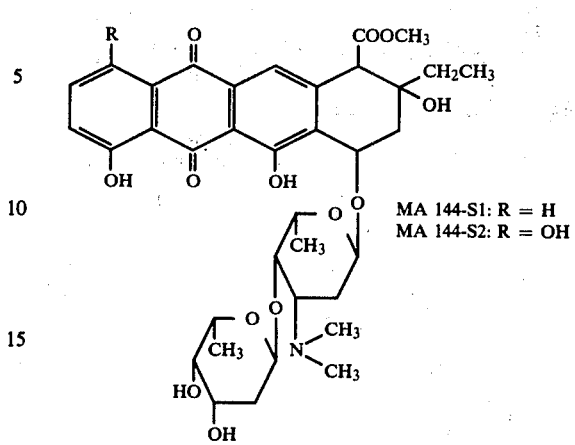

MA 144-S1: R = H
MA 144-S2: R = OH

MA 144-N1 consists of aklavinone and three kinds of sugar moieties; L-rhodosamine, 2-deoxy-L-fucose and L-rhodinose. In order to determine the sugar sequence, mild hydrolysis in 0.5% hydrochloric acid at room temperature for 10 min. was carried out according to the method of Biedermann et al. (Pharmazie, 27, 782–789, 1972). L-rhodinose was liberated and simultaneously MA 144-S1 was formed. Thus, the chemical structure of MA 144-N1 was determined to be as follows:

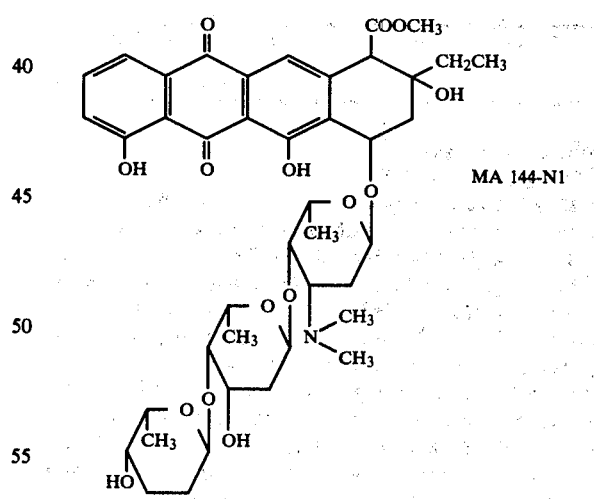

MA 144-N1

MA 144-U1 and -U2 contain two kinds of sugar moieties; L-rhodosamine and 2-deoxy-L-fucose. Furthermore, on methanolysis, methyl 2-deoxy-L-fucosyl-2-deoxy-L-fucoside, which was determined by NMR and $^{13}$C-NMR spectra, and 1-deoxypyrromycin or pyrromycin were formed, and thus the following chemical structure was proposed.

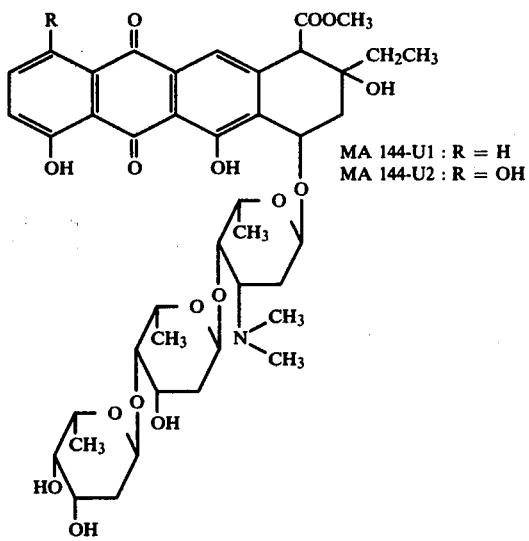

MA 144-U1 : R = H
MA 144-U2 : R = OH

MA 144-Y consists of aklavinone and three kinds of sugar moieties; L-rhodosamine, 2-deoxy-L-fucose and a previously unreported sugar. Furthermore, 1-deoxypyrromycin and an unknown methylated disaccharide were obtained from MA 144-Y by methanolysis. The said methylated disaccharide was extracted with ether and purified by silicic acid and Sephadex LH-20 (Trademark) column chromatography, and then crystallized as white needle crystals in benzene. Physicochemical properties of the said methylated disaccharide are as follows:

Elemental analysis:

| Found | % | Calcd. | % |
|---|---|---|---|
| | C = 57.77 | | C = 57.34 |
| | H = 7.31 | | H = 7.40 |
| | | for $C_{13}H_{20}O_6$ | |

Molecular weight: 272
Melting point: 109°–110° C.
Optical rotation: $[\alpha]_D^{22} = -65°$ (c=1.0, CHCl$_3$)
Ultraviolet and visible light absorption spectra in methanol $\lambda_{max}^{MeOH}$ nm ($\epsilon$)=209 (6726)
The methyl disaccharide of MA 144-Y has an infrared absorption peak at 1680 cm$^{-1}$ and UV absorption maximum at $\lambda_{max}^{MeOH}$ nm ($\epsilon$): 209 (6726) indicating the presence of the $\alpha$, $\beta$ unsaturated keto group. From proton NMR, a three-proton doublet at $\delta$1.26 (J=6.8 Hz), a two-proton at $\delta$1.9, a one-proton doublet at $\delta$3.74 (J=1 and 3 Hz), a one-proton quartet at $\delta$3.94 (J=6.8 Hz), a one-proton at $\delta$4.07 and a one-proton at $\delta$4.8 were assigned to the nine protons consisting of 2-deoxy-L-fucose, and a three-proton doublet at $\delta$1.4 (J=6.8 Hz) and a one-proton symmetrical quartet at $\delta$4.73 (J=6.8 Hz) deshielded by the ethereal oxygen atom were coupled with each other, and were assigned to the methyl protons at C-6' and the proton at C-5', respectively. By spin decoupling experiments, a doublet at $\delta$6.86 (J=3.5 and 10.0 Hz) and two doublets at $\delta$6.11 (J=10.0 Hz) and $\delta$5.26 (J=3.5 Hz) were assigned to the vinyl protons of the ABM system, corresponding to the protons at C-2', C-3' and C-1', respectively. Thus, the sugar moiety other than 2-deoxy-L-fucose in the methyl dissacharide was identified as 2,3,6-trideoxyhex-2-enopyranos-4-ulose which was attached to C-4 of 2-deoxy-L-fucose.

From the results analysed above, the structure of the methylated disaccharide was determined to be a new sugar:

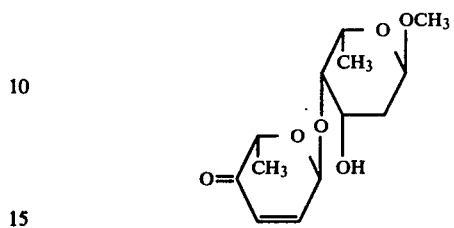

and the new terminal sugar was named aculose.

Thus, the chemical structure of MA 144-Y in the present invention was determined to be as follows:

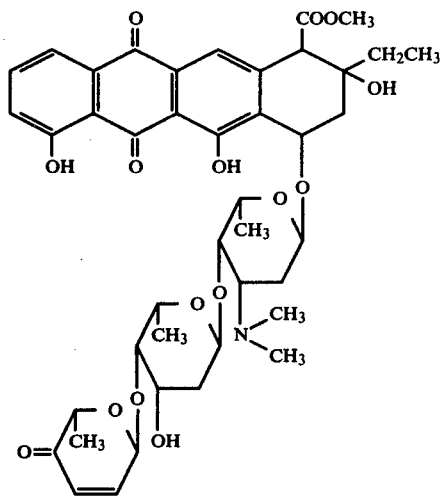

While a number of anthracycline glycoside antibiotics having aklavinone and $\epsilon$-pyrromycinone aglycone moieties are known in the art, the compounds MA 144-G1, -G2, -L, -N1, -S1, -U1 and -Y are clearly different from any of them in such characteristics as molecular formula, degradation products on acid hydrolysis, ultraviolet, visible, infrared and NMR spectra and the like, as described above. Among the known anthracycline glycosides, aklavin and pyrromycin consist of aklavinone or $\epsilon$-pyrromycinone and one sugar, L-rhodosamine, thus distinguishing them from the compounds in the present invention. Aclacinomycin A and cinerubin A consist of three sugar moieties; L-cinerulosyl-2-deoxy-L-fucosyl-L-rhodosaminyl, MA 144-M1 and -M2 (U.S. patent application Ser. No. 780,730 now U.S. Pat. No. 4,144,329) consist also of three sugar moieties; L-amicetosyl-2-deoxy-L-fucosyl-L-rhodosaminyl, and rhodirubin B [J. Antibiotics 30(7):616–618 (1977)] consists of L-rhodinosyl-L-rhodinosyl-L-rhodosaminyl. These three known antibiotics are distinguished from the compounds of the present invention on the basis of sugar moiety. The sugar moiety of rhodirubin A consists of L-rhodinosyl-2-deoxy-L-fucosyl-L-rhodosaminyl which is the same as that of MA 144-N1 in the present invention, but the aglycone of MA 144-N1 is aklavinone and thus different from the $\epsilon$-pyrromycinone of rhodirubin A.

Thus it is verified that MA 144-G1, -G2, -L, -N1, -S1, -U1 and -Y in the present invention are novel substances.

Antimicrobial Activity of MA 144 Components

MA 144-G1, -G2, -L, -S1, -S2, -N1, -U1, -U2 and -Y exhibit antimicrobial activities against various kinds of microorganisms. The minimum inhibitory concentration of the present antibiotics as determined by the broth dilution method are shown in the following table.

the compounds in the present invention showed marked inhibitory effects on mouse leukemia L1210. For example, BDF$_1$ mice weighing 19-22 g. were inculated intraperitoneally with $1 \times 10^6$ L1210 cells/mouse and 24 hrs. after inoculation the test compound was intraperitoneally injected once daily for 9 days consecutively. On day 30, the % of prolongation of the survival time to control was shown in the following table with their LD$_{50}$ values upon a single intraperitoneal injection in dd mice.

| | Antimicrobial Spectrum of MA 144 Components MIC (meg./ml) MA 144- | | | | | | | | |
|---|---|---|---|---|---|---|---|---|---|
| Test Microorganism | G1 | G2 | L | N1 | S1 | S2 | U1 | U2 | Y |
| Staph. aureus FDA 209P | 6.25 | 3.12 | 6.25 | 6.25 | 6.25 | 6.25 | 6.25 | 3.1 | 0.4 |
| Staph. aureous Smith | 1.56 | 1.56 | 1.56 | 0.78 | 3.1 | 0.78 | 3.1 | 0.78 | 0.2 |
| Bac. subtilis ATCC 6633 | 3.12 | 1.56 | 3.1 | 3.1 | 3.1 | 3.1 | 3.1 | 3.1 | 0.2 |
| Bac. cerous ATCC 9634 | 1.56 | 0.78 | 1.56 | 0.78 | 1.56 | 0.78 | 1.56 | 1.56 | 0.1 |
| Bac. magaterium NRRL B-938 | 6.25 | 6.25 | 6.25 | 3.1 | 3.1 | 3.1 | 3.1 | 1.56 | 0.2 |
| Sar. lutea ATCC 9341 | 0.78 | 0.78 | 0.78 | 0.78 | 1.56 | 1.56 | 1.56 | 1.56 | 0.2 |
| Mic. flavus | 0.2 | 0.2 | 0.2 | 0.4 | 1.56 | 0.78 | 1.56 | 0.78 | 0.1 |
| Corv. bovis 1810 | 1.56 | 0.78 | 1.56 | 0.78 | 0.78 | 0.78 | 6.25 | 6.25 | 0.2 |
| Ps. fluorescens NIHJB-254 | 100 | 100 | 100 | >100 | >100 | >100 | >100 | >100 | >100 |
| Pr. morganii | >100 | >100 | >100 | >100 | >100 | >100 | >100 | >100 | >100 |
| Mycobact. smegmatis ATCC 607 | 3.12 | 3.12 | 3.1 | >100 | >100 | >100 | >100 | >100 | 3.1 |
| Can. albicans IAM 4905 | 100 | >100 | 100 | >100 | >100 | >100 | >100 | >100 | >100 |
| Can. tropicalis IAM 4942 | 100 | >100 | 100 | >100 | >100 | >100 | >100 | >100 | >100 |

As shown above, MA 144 components in the present invention possess antimicrobial activity, especially against gram-positive bacteria, and thus they are therapeutically useful in the treatment of mammals for diphtheria, tuberculosis, pneumonia, tetanus and other infectious diseases caused by gram-positive bacteria.

Antitumor Activity and Acute Toxicity of MA 144 Components

MA 144 components in the present invention show a marked antitumor activity with low toxicity in experimental animal tests and thus are therapeutically useful in inhibiting the growth of animal tumors. In particular, Therapeutic Effectiveness against Mouse Leukemia L1210 and Toxicity of MA 144 Components

| | Prolongation of the survival time (% T/C) MA 144- | | | | | | | | |
|---|---|---|---|---|---|---|---|---|---|
| Compounds | G1 | G2 | L | N1 | S1 | S2 | U1 | U2 | Y |
| Anti-L1210 activity Dose (mg./kg./day) | | | | | | | | | |
| 20 | — | — | — | — | — | — | — | — | 65 |
| 10 | — | — | 135 | 108 | 98 | — | 90 | — | 143 |
| 5 | 187 | 90 | 128 | 200 | 140 | 85 | 127 | 86 | 127 |
| 2.5 | 215 | 130 | 114 | 184 | 168 | 110 | 165 | 86 | 115 |
| 1.25 | 145 | 164 | 95 | 137 | 133 | 145 | 157 | 112 | — |
| 0.6 | 130 | 140 | — | 123 | 114 | 130 | 129 | 135 | — |
| 0.3 | 118 | 108 | — | 110 | 96 | 118 | 114 | 129 | — |
| 0.15 | 101 | 97 | — | — | — | 97 | — | 110 | — |
| Toxicity (mouse) Intraperitoneal administration (mg./kg.) | | | | | LD$_{50}$ | | | | |
| | 28.5 | 17.0 | 45.5 | 32.5 | 24.4 | 12.5 | 30.2 | 14.5 | 40-50 |

Cytotoxicity against Cultured L1210 Cells of MA 144 Components

MA 144 components in the present invention inhibited the growth of mammalian tumor cells in culture, especially at low concentration, and completely inhibited RNA synthesis. In this experiment, L1210 cells were inoculated in RPMI 1640 medium (Nissui, Rosewell Park Memorial Institute 1640) containing 20% calf serum and cultivated at 37° C. for 3 days in a CO$_2$ incubator, and the test compounds then were added at a concentration of 0.1 μg./ml. on day 1. In the $^{14}$C-incorporation experiment, the compounds in the present invention were added at a concentration of 0.5 μg./ml. for RNA synthesis and at 1.0 μg./ml. for DNA synthesis, and also $^{14}$C-thymidine or -uridine was added to the medium for 60 min. at 37° C. Effects on the growth and the synthesis of DNA and RNA were indicated by the inhibition percent to the control as shown in the following table. From the results, MA 144 components inhibited markedly the growth and RNA synthesis of cultured L1210 cells at low concentration. These results support the therapeutic effectiveness on animal experimental tumors.

Effects of MA 144 Components on the Growth and Macromolecular Synthesis in Cultured L1210 Cells

| Compounds | Growth (on Day 2) | % Inhibition Synthesis of RNA | DNA |
|---|---|---|---|
| Aclacinomycin | 89.7 | 81.6 | 69.6 |
| MA 144-G1 | 80.7 | 65.6 | 40.9 |
| -G2 | 82.1 | 57.8 | 39.4 |
| -L | 27.4 | 39.7 | 11.3 |
| -N1 | 79.2 | 74.4 | 57.4 |
| -S1 | 86.0 | 74.1 | 76.5 |
| -S2 | 88.1 | 65.6 | 48.8 |
| -U1 | 78.5 | 67.2 | 27.7 |
| -U2 | 80.5 | 71.5 | 30.5 |
| -Y | 90.2 | 93.9 | 99.6 |

The Therapeutic Use of MA 144 Components

As mentioned above, the components MA 144-G1, -G2, -L, -N1, -S1, U1 and -Y in the present invention are novel antibiotics, useful in both human and veterinary medicine, and also possess marked inhibitory action against solid and ascitic-type malignant tumors in experimental animals. This invention, therefore, provides a method for the inhibition in experimental animals of malignant tumors which comprises administering to said host an amount, effective for inhibiting said tumor, of MA 144-G1, -S1, -N1, -U1, -Y, -G2 or -L, or a non-toxic acid addition salt or deoxyribonucleic acid complex thereof.

The invention includes within its scope pharmaceutical compositions containing an effective antibacterial or tumor-inhibiting amount of at least one of such antibiotic compounds mentioned above, or a non-toxic acid addition salt or deoxyribonucleic acid complex thereof, with an inert pharmaceutically acceptable carrier or diluent. The compositions may be made up in any pharmaceutical form appropriate for the route of administration. Examples of such compositions include solid compositions for oral administration such as tablets, capsules, pills, powders and granules, liquid compositions for oral administration such as solutions, suspensions, syrups and elixers and preparations for parenteral administration such as sterile solutions, suspensions or emulsions.

The compounds in the present invention form non-toxic acid addition salts with a variety of organic and inorganic salt-forming reagents and form non-toxic complexes with deoxyribonucleic acid. Thus, acid addition salts formed with such pharmaceutically acceptable acids as sulfuric, phosphoric, hydrochloric, acetic, propionic, oleic, palmitic, citric, succinic, tartaric, glutamic, pantothenic, etc. and non-toxic complexes with deoxyribonucleic acid can be employed in the same manner as the MA 144 components per se. The salts are formed, isolated, purified and formulated by the methods generally employed in salt formation for antibiotics, particularly anthracycline glycoside antibiotics. For example, the chosen antibiotic and acid may be mixed in an appropriate solvent such as ethyl acetate, acetone or toluene and the resulting salt obtained by lyophilization or by precipitation. In applying the antibiotics of the present invention, a non-toxic complex such as a DNA complex is also useful therapeutically. In this case DNA extracted from animals or microorganisms such as calf thymus, HeLa cells, human and animal embryonic cells, yeasts, etc. can be used. Preparation of DNA-MA 144 complexes can be carried out by methods described in the literature for preparing DNA complexes of other anthracycline antibiotics such as adriamycin, daunorubin, etc. [see, for example, Nature, New Biol. 239:110 (1973) and Europ. J. Cancer 10:399 (1974)]. For purposes of this invention, the compounds in the free base form are equivalent to their non-toxic acid addition salts and complexes.

It will be appreciated that the actual preferred amounts of the compounds in the present invention used will vary according to the particular compound being used, the particular composition formulated, the mode of application and the particular situs, host and disease being treated. In general the MA 144 components are injected intraperitoneally, intravenously, subcutaneously or locally, or administered orally. Many factors that modify the action of the drug will be taken into account by those skilled in the art, for example, age, body weight, sex, diet, time of administration, route of administration, rate of excretion, condition of the patient, drug combinations, reaction sensitivities and severity of the disease. Administration can be carried out continuously or periodically within the maximum tolerated dose. Optimal application rates for a given set of conditions can be ascertained by those skilled in the art using conventional dosage determination tests in view of the above guidelines.

For use as an antibacterial agent, the MA 144 components are in general administered so that the concentration of active ingredient is greater than the minimum inhibitory concentration for the particular organism being treated.

The following examples are provided for illustrative purposes only and are not intended to limit the scope of the invention.

Preparation of Starting Materials

I. MA 144-M1 and -M2

A. MA 144-M2—enzymatic conversion of cinerubin A

A mixture of the livers isolated from 10 Wister rats (300 g., ♂) and 10 volumes of 10 mM Tris buffer (pH 7.8) containing 10 mM magnesium chloride and 0.25 M sucrose was homogenized by a Teflon homogenizer and centrifuged at 10,000 rpm. for 20 min. The supernatant (400 ml.) obtained was mixed with 50 ml. of 5 mg./ml. cinerubin A and 50 ml. of 6 mg./ml. NADP, distributed 50 ml. each in 500 ml.-flasks, and incubated at 40° C. for 1 hr. on a rotary shaker. Reaction was stopped by the addition of two volumes of cold chloroform-methanol (1:1) mixture. This solution was mixed well and separated from the chloroform layer, and the remaining active fraction in the aqueous layer was re-extracted with an equal volume of chloroform.

Both chloroform layers were combined, concentrated under reduced pressure, applied onto silicic acid thin-layer plates and developed with chloroform-methanol (10:1) mixture for preparation. After chromatography, the band corresponding to MA 144-M2 was scratched off and MA 144-M2 was extracted with methanol, concentrated under reduced pressure and crystallized from a chloroform-n-hexane mixture. There was obtained 51.3 mg. of red needle crystals of MA 144-M2.

B. MA 144-M1—enzymatic conversion of aclacinomycin A

Using mouse liver homogenates as an enzyme source, 100 mg. of aclacinomycin A was treated according to the same procedure as described in Preparation IA (coenzyme used was NADP), and 48.5 mg. of MA 144-M1 was obtained as a yellow powder.

C. MA 144-M2 and -M1—enzymatic conversion

Using fresh rabbit liver slices as an enzyme source, 200 mg. of the mixed substrate including 35.5 mg. cinerubin A and 112.5 mg. aclacinomycin A was incubated with liver splices and coenzyme NADP in 1000 ml. of a magnesium-sucrose-Tris solution (pH 7.8) as described in Preparation IA.

The reaction mixture was extracted with chloroform, and 20 ml. of 1% $CuSO_4.5H_2O$ was added to the chloroform layer (100 ml.). After the solution was shaken vigorously, $10^{-3}$ M EDTA solution was added to the chloroform layer separated from the aqueous layer and shaken vigorously, and the chloroform layer was then washed by shaking twice with a small amount of water. The chloroform extract was concentrated, and 51 mg. of MA 144-M1 yellow powder was obtained by the addition of n-hexane. The initial aqueous layer containing the precipitation of $Cu^{++}$-chelated MA 144-M2 complex was centrifuged, and the precipitate was washed with acetone, dissolved in 10 ml. of 0.1 N HCl, and extracted with an equal volume of ethyl acetate. The extract was washed twice with NaCl-saturated water, washed with water again, and concentrated under reduced pressure. By the addition of n-hexane to the concentrate, 10.5 mg. of MA 144-M2 was obtained as a red powder.

D. MA 144-M1—chemical reduction of aclacinomycin A

One gram of aclacinomycin A was dissolved in 40 ml. of ethyl acetate, mixed with 40 ml. water containing 100 mg. of sodium borohydride, and shaken vigorously for 20 min. at room temperature in a separatory funnel. The reaction mixture was allowed to stand and separate from the ethyl acetate layer, and the extract was washed with the NaCl-saturated solution containing $10^{-5}$ M EDTA, washed twice with water, and then concentrated after dehydration with anhydrous sodium sulfate. After silicic acid column chromatography (3×20 cm.) using toluene-methanol mixture (100:3), active fractions containing MA 144-M1 were pooled, concentrated, and added to n-hexane. The resultant yellow precipitate of MA 144-M1 weighed 450 mg.

E. MA 144-M2—chemical reduction of cinerubin A

Cinerubin A (2 g.) was dissolved in 80 ml. of ethyl acetate-chloroform-methanol mixture (10:1:1), mixed with 80 ml. water containing 200 mg. of sodium borohydride, and shaken vigorously for 20 min. at room temperature in a separatory funnel. Further purification was carried out according to Preparation ID and 760 mg. of MA 144-M2 was obtained from ethyl acetate-n-hexane as red needle crystals.

F. MA 144-M1 and -M2—fermentation

A nutrient medium having the following composition was prepared:

| Potato starch | 2% w/v |
| --- | --- |
| Glucose | 2 |
| (Trademark of "Meat" Soybean Powder) | 2.5 |
| $KH_2PO_4$ | 0.1 |
| $K_2HPO_4$ | 0.1 |
| $MgSO_4 . 7H_2O$ | 0.1 |
| NaCl | 0.3 |
| $MnCl_2 . 4H_2O$ | 0.0005 |
| $FeSO_4 . 7H_2O$ | 0.0005 |
| Silicone | 0.005 (pH 7.2) |

Fifty ml. of this medium was sterilized at 120° C. for 15 min. in a 500 ml.-flask which was inoculated with one ml. of frozen culture of *Streptomyces galilaeus* MA 144-M1 (FERM P-2455) and incubated at 30° C. for 48 hours on a rotary shaker. Ten liters of the previously sterilized medium in a 20 liter stainless steel jar fermentor were aseptically inoculated with 200 ml. of the above seed culture. Fermentation was carried out at 30° C. for 18 hrs. with agitation (300 rpm) and aeration (5 l/min.). Then, 10 liters of this culture were transfered to 600 liters of the previously sterilized medium in a 1 Kl-stainless steel tank as the second seed, and cultured at 30° C. for 48 hrs. with agitation (180 rpm) and aeration (200 l/min.).

The cultured broth obtained (570 liters) was adjusted to pH 5.0 with sulfuric acid and filtered with diatomaceous earth. The resulting filtered cake (54 kg.) was suspended in 7 liters of acetone and filtered after stirring for 3 hrs. The residue was re-extracted with 85 l of acetone. Both extracts were concentrated to 40 liters under reduced pressure, added to 25 liters of ethyl acetate, and stirred. After separating the ethyl acetate layer and concentrating to 1 liter under reduced pressure, crude aclacinomycin A mixture was precipitated by addition of n-hexane to the concentrate, and then 16 grams of orange yellow powder were obtained after washing twice with a n-hexane-ethyl acetate mixture (50:1).

This crude powder was dissolved in 200 ml. of ethyl acetate, applied onto a column filled with 700 grams of Column-Lite (Trademark of Fuji Chemical Co. for silicic acid), and eluted with an ethyl acetate-methanol mixture (1:1). The yellow eluate was concentrated to dryness under reduced pressure. The crude aclacinomycin powder obtained (12 g.) was dissolved in 100 ml. of chloroform, shaken with 50 ml. of $10^{-3}$ M EDTA-0.01 M phosphate buffer (pH 6.8) to remove residual metal ions, and the chloroform layer was washed twice with water, dried with anhydrous sodium sulfate and then concentrated to dryness under reduced pressure. There was obtained 11 grams of yellow powder containing aclacinomycin A.

This powder was dissolved in a small amount of toluene, applied to a silicic acid column (4×40 cm.), and eluted. Aclacinomycin A, B and other impurities were eluted with 2% (v/v) methanol-containing toluene and then the MA 144-M1 fraction was eluted with 3% methanol-containing toluene and concentrated to dryness to give 10.5 mg. of MA 144-M1 as a yellow powder.

The above-mentioned Column-Lite column after elution of the yellow fractions was treated with $10^{-3}$ M EDTA-containing 30% (v/v) methanol mixture, and the resulting red eluate was evaporated to dryness to give 5.0 grams of red powder containing cinerubin A. This red powder was treated with EDTA and chromatographed by a silicic acid acid column as described for MA 144-M1. There was obtained 6.2 mg. of MA 144-M2 as a red powder.

The following are physiochemical properties of MA 144-M1 an MA 144-M2:

MA 144-M1

Weakly basic, lipophilic and yellow powder. Elemental analysis yields the following values:

| Found | | Calcd. | |
|---|---|---|---|
| | C = 62.37 | | C = 61.98 |
| | H = 7.08 | | H = 6.81 |
| | O = 28.81 | | O = 29.49 |
| | N = 2.07 | | N = 11 1.72 |
| | | for $C_{42}H_{55}O_{15}N$ | |
| Molecular weight = 814 | | | |

The melting point and specific rotation ($[\alpha]_D^{20}$ of its 1% solution in chloroform) exhibit 149° to 150° and +40°, respectively. Its absorption spectra in the ultraviolet and in the visible range in methanol show maxima at the following wave-lengths:

| | $\lambda_{max}( E_1^{1\%}{}_{cm})$ |
|---|---|
| in MeOH | 229(775), 258(335), 290(128), 432(155) |
| in 0.01N HCl-MeOH | 229(815), 259(345), 290(130), 432(160) |
| in 0.01N NaOH-MeOH | 237(575), 250$_s$(405), 290(125), 323$_s$(80), 526(135) |

$_s$: shoulder

MA 144-M1 is soluble in acidic water, dimethyl sulfoxide, methylcellosolve, methanol, ethanol, ethyl acetate, acetone, chloroform, benzene, toluene and slightly soluble in water, diethyl ether and n-hexane. On the other hand, the hydrochloride salt is soluble in water, methanol and chloroform, but slightly soluble in acetone and ethyl acetate. The methanol solution of MA 144-M1 is yellow in conc. HCl, but turns to reddish brown in concentrated sulfuric acid. With alcoholic magnesium acetate, the solution shows a red color and turns to reddish purple on alkalinization. MA 144-M gives a negative ninhydrin reaction and does not reduce Fehling solution.

MA 144-M2

Weakly basic, lipophilic and red needle crystals. Elemental analysis yields the following values:

| Found | | Calcd. | |
|---|---|---|---|
| | C = 60.43 | | C = 60.79 |
| | H = 6.74 | | H = 6.68 |
| | O = 29.70 | | O = 30.84 |
| | N = 1.75 | | N = 1.69 |
| | | for $C_{42}H_{55}O_{16}N$ | |
| Molecular weight = 830 | | | |

The melting point is 151° to 152° C. and the specific-rotation ($[\alpha]_D^{20}$ of 1% solution in chloroform) exhibits +127°. The absorption spectra in the ultraviolet and in the visible ranges show maxima at the following wavelengths:

| | $\mu_{max}(E_1^1{}_{cm})$ |
|---|---|
| in MeOH | 235(600), 259(310), 269(170), 291(105), 492(165). |
| in 0.01N HCl-MeOH | 235(615), 259(325), 269(185), 291(115), 492(170). |

MA 144-M2 is soluble in acidic water, dimethyl sulfoxide, methyl cellosolve, chloroform, ethyl acetate, methanol, ethanol, acetone, benzene, and slightly soluble in water, n-hexane, cyclohexane, diethyl ether and petroleum ether. The hydrochloride salt is soluble in water, methanol, ethanol and chloroform, but slightly soluble in acetone and ethyl acetate. MA 144-M2 gives a negative ninhydrin reaction and does not reduce Fehling solution.

The methanol solution is red in concentrated hydrochloric acid and turns to violet in concentrated sulfuric acid. The solution appears reddish purple in alcoholic magnesium acetate, and gives purplish blue in NaOH solution.

MA 144-M1 and -M2 have the following structures:

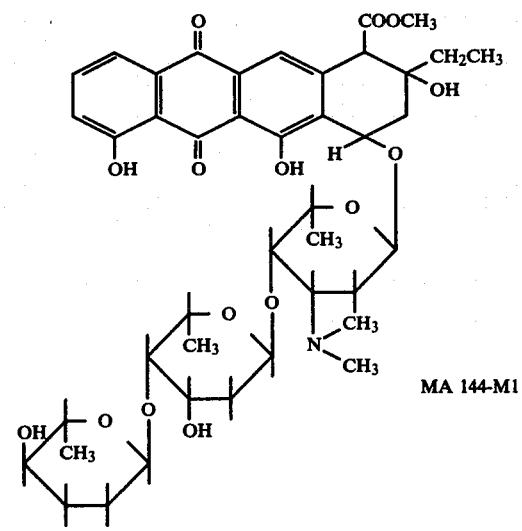

MA 144-M1 and

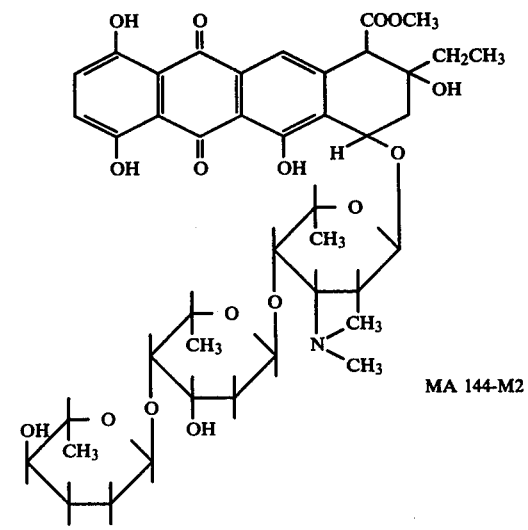

MA 144-M2

II. Rhodirubin A

A nutrient medium having the following composition was prepared:

| Potato starch | 1 | % (w/v %) |
|---|---|---|
| Glucose | 1 | % |
| "Prorich" (soybean powder) | 1.5 | % |
| $K_2HPO_4$ | 0.1 | % |
| $MgSO_4 \cdot 7H_2O$ | 0.1 | % |
| NaCl | 0.3 | % |
| Mineral* | 0.125 | % (pH 7.4) |

*Mineral is consisted of as follows:
| $CuSO_4 \cdot 5H_2O$ | 2.8 g. |
|---|---|
| $FeSO_4 \cdot 7H_2O$ | 0.4 g. |
| $MnCl_2 \cdot 4H_2O$ | 3.2 g. |
| $ZnSO_4 \cdot 7H_2O$ | 0.8 g. |
| in 500 ml. of water. | |

Fifty ml. of this medium was sterilized in a 500 ml.-flask, inoculated with a loop from the agar slant of *Streptomyces galilaeus* (ATCC 31133) and incubated at 28° C. for 48 hours on a rotary shaker (230 rpm) to obtain the seed culture.

The following medium was then prepared:

| Potato starch | 2 | % (w/v %) |
|---|---|---|
| Glucose | 2 | % |
| "Nisshin toast" (defatted soybean) | 2 | % |
| Yeast extract | 0.5 | % |
| NaCl | 0.25 | % |
| $CaCO_3$ | 0.3 | % |
| Mineral* | 0.125 | % (pH 7.4) |

*Mineral is consisted of as follows:
| $CuSO_4 \cdot 5H_2O$ | 1.25 g. |
|---|---|
| $MnCl_2 \cdot 4H_2O$ | 1.25 g. |
| $ZnSO_4 \cdot 7H_2O$ | 1.25 g. |
| in 500 ml. of water. | |

Two ml. of said seed culture was then inoculated into 100 ml. of the previously sterilized medium described immediately above in a 500 ml.-flask. Fermentation was carried out at 28° C. on a rotary shaker (230 rpm), and the production of rhodirubin attained a maximum after 4 days. The broth was filtered to separate mycelial cake and filtrate. One-half volume of chloroform was added to the filtrate and the extraction was carried out twice. Acetone was added to the mycelial cake (2 L. of acetone/1 kg. of wet cake) and the extraction was carried out twice, after which the acetone was removed by evaporation under reduced pressure. One-half volume of chloroform was added to the residue and the extraction was carried out twice. The chloroform extracts obtained were combined with the chloroform extracts from the filtrate and concentrated under reduced pressure to obtain a tar-like substance. Said substance was dissolved in a small amount of ethyl acetate, and a precipitate was formed by the dropwise addition of this solution into 10 volumes of n-hexane (4.5 g. of red crude powder was obtained). This crude powder was dissolved in 30 ml. of a mixture of toluene and methanol (50:1) (v/v), applied onto a column (3×50 cm.) filled with 100 g. of silica gel which equilibrated with the same mixture, and rhodirubin B and then rhodirubin A were eluted. Each eluate was dried under reduced pressure to obtain 27 mg. of crude rhodirubin A and 60 mg. of crude rhodirubin B.

Physicochemical properties of rhodirubin A are as follows:

Red powder having a melting point of 141°–143° C.
Elementary analysis yields the following values:

|  | Found | Calcd for $C_{42}H_{55}NO_{16}$ |
|---|---|---|
|  | C = 60.39% | C = 60.77% |
|  | H = 6.63% | H = 6.68% |
|  | O = 30.72% | O = 30.81% |
|  | N = 1.71% | N = 1.69% |

Molecular weight: 829.9

Specific rotation: $[\alpha]_D^{20} + 120$ (C=0.1, $CHCl_3$)

Solubility: Rhodirubin A is soluble in methanol, n-butanol, acetone, ethyl acetate, chloroform, toluene, benzene and dimethylsulfoxide, insoluble in water, n-hexane and petroleum ether and slightly soluble in diethyl ether.

Color and reaction: The methanol solution of rhodirubin A is red, but turns to reddish purple in the alkaline state. It gives a negative ninhydrin reaction and does not reduce Fehling solution.

Absorption spectrum: Ultraviolet and visible absorption maxima are seen at 235 nm, $E_{1cm}^{1\%}=507$; 258 nm, $E_{1cm}^{1\%}=267$; 295 nm, $E_{1cm}^{1\%}=100$; 457 nm, $E_{1cm}^{1\%}=127$; 490 nm, $E_{1cm}^{1\%}=153$; 510 nm, $E_{1cm}^{1\%}=117$; 522 nm, $E_{1cm}^{1\%}=100$ (in methanol at a concentration of 15 mcg./ml.)

Absorption spectrum: Infrared

The IR spectrum in KBr shows peaks at the following wavelengths in $cm^{-1}$: 3430, 2950, 2930, 2810, 2750, 1735, 1640, 1600, 1450, 1320, 1300, 1220, 1160, 1120, 1040, 1000, 970, 960, 920, 800 and 760.

NMR: The PMR spectrum of rhodirubin A in $CDCl_3$ (100 MHz) shows the following chemical shifts (ppm): 7.6, s; 7.24, s; 5.50 m; 5.62, m; 5.02, m; 4.84, m; 4.52, q; 4.7~3.90, overlapping m; 3.72, s; 3.60~0.09, overlapping m and 2.18.

Rhodirubin A has the structure:

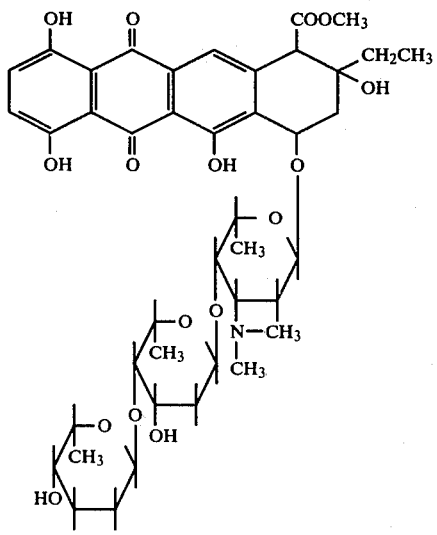

EXAMPLE 1

A nutrient medium having the following composition was prepared:

| | | |
|---|---|---|
| Glucose | 2 | % (w/v %) |
| Potato starch | 2 | % |
| "Meat" (Trademark of Ajinomoto Co. for soybean powder) | 2 | % |
| K$_2$HPO$_4$ | 0.1 | % |
| MgSO$_4$ . 7H$_2$O | 0.1 | % |
| NaCl | 0.3 | % |
| MnCl$_2$ . 4H$_2$O | 0.0008 | % |
| CuSO$_4$ . 7H$_2$O | 0.0007 | % |
| FeSO$_4$ . 7H$_2$O | 0.0001 | % |
| ZnSO$_4$ . 7H$_2$O | 0.0002, | pH 7.2 |

Fifty ml. of this medium was sterilized at 120° C. for 15 min. in a 500-ml. flask, inoculated with one ml. of frozen culture of *Streptomyces galilaeus* MA 144-M1 (FERM P-2455, ATCC 31133) and incubated at 30° C. for 48 hrs. on a rotary shaker to obtain a seed culture. Ten liters of previously sterilized nutrient medium in a 20-liter stainless steel jar fermentor were aseptically inoculated with 200 ml. of the above seed culture. Fermentation was carried out at 28° C. for 18 hrs. with agitation (300 rpm) and aeration (5 l/min.). Then, 10 liters of this culture were transfered to 600 liters of previously sterilized medium in a 2-kl. stainless steel tank and cultured at 28° C. for 36 hrs. with agitation (180 rpm) and aeration (300 l/min.).

The cultured broth obtained (580 l.) was adjusted to pH 5.0 with sulfuric acid and filtered with diatomaceous earth. The resulting filtered cake (56 kg.) was suspended in 50 liters of acetone and filtered after stirring for 1 hr. The residue was re-extracted with 50 liters of acetone. Both extracts were concentrated to 25 liters under reduced pressure, added to 20 liters of ethyl acetate, and stirred. After separating the ethyl acetate layer and concentrating to 1 liter under reduced pressure, crude MA 144 mixture was precipitated by addition of 15 l of n-hexane to the concentrate. Thirty six grams of MA 144 red powder (MA 144 mixture) were obtained after washing twice with n-hexane. The culture filtrate obtained above was adjusted to pH 6.8 with sodium hydroxide and extracted with 100 liters of toluene. The extract was concentrated to 10 liters under reduced pressure and reextracted with 10 liters of acetate buffer at pH 3.5. The aqueous layer obtained was adjusted to pH 6.8, extracted again with 4 liters of toluene and then concentrated to 30 ml. under reduced pressure. Crude MA 144 mixture was precipitated by addition of 300 ml. of n-hexane to the concentrate and 2.5 additional grams of red powder were obtained.

EXAMPLE 2

The crude powder of MA 144 mixture obtained from the filtered cake as in Example 1 (10 grams) was dissolved in 100 ml. of toluene and subjected to a column (5×40 cm.) filled with 300 g. of silicic acid. After discarding the initial eluate with 1.5% methanol-containing toluene, MA 144-G1, -G2 and -L fractions were successively eluted with 2% methanol-containing toluene. The MA 144-N1 fraction was then eluted with 3% methanol-containing toluene, and MA 144-S1 and -S2 fractions and MA 144-U1 and -U2 fractions were eluted with 5% methanol-containing toluene, successively. After concentrating each fraction obtained above, crude orange-red powders of 210 mg. MA 144-G1 and -G2 mixture, 190 mg. MA 144-L, 570 mg. MA 144-N1 and rhodirubin A mixture, 360 mg. MA 144-S1 and -S2 mixture and 270 mg. MA 144-U1 and -U2 mixture were obtained by addition of n-hexane.

EXAMPLE 3

The crude powder of MA 144 mixture (2.5 g.) obtained from the culture filtrate as in Example 1 was dissolved in 6 ml. of toluene, subjected to a column filled with 100 g. of silicic acid, and the MA 144-Y fraction eluted with 1.7% methanol-containing toluene at 5° C. The resulting fraction was concentrated to dryness under reduced pressure to give 400 mg. of crude MA 144-Y as an orange-red powder.

EXAMPLE 4

MA 144-G1 and -G2 mixture (210 mg.) obtained in Example 2 was dissolved in a small amount of ethyl acetate and subjected to a column filled with 30 g. of "Column-Lite" (Trademark, Fuji Cem. Co. for silicic acid), and eluted with an ethyl-acetate-methanol mixture (1:1) (v/v). The yellow fraction was concentrated to dryness under reduced pressure, and the residue obtained was dissolved in 50 ml. of chloroform, shaken with 50 ml. of 0.01 M phosphate buffer containing 10$^{-3}$M EDTA to remove the residual metal ions, and the chloroform layer washed twice with water, dried with anhydrous sodium sulfate and then concentrated to dryness under reduced pressure. There was obtained 110 mg. of a yellow powder of MA 144-G1.

The above-mentioned "Column-Lite" column after elution of the yellow fractions was treated with 10$^{-3}$M EDTA-containing 30% methanol mixture. The resulting red eluate was evaporated to dryness, dissolved in a small amount of chloroform and treated according to the above-mentioned method to remove residual metal ions. There was obtained 22 mg. of MA 144-G2 as a red powder.

Crude powder of MA 144-L in Example 2 was treated in the same manner as described above for MA 144-G1, and 115 mg. of yellow powder of MA 144-L was obtained. By the same refining procedure of MA 144-G1 and -G2 as described above, purified powders of 260 mg. of MA 144-N1, 150 mg. of MA 144-S1, 88 mg. of MA 144-S2, 128 mg. of MA 144-U1, 54 mg. of MA 144-U2 and 114 mg. of MA 144-Y were obtained.

EXAMPLE 5

According to the general method of Examples 1, 2 and 4, the compounds in the present invention were obtained as follows using the indicated Streptomyces strains:

| Strains | MA 144 obtained (mg.) | | | | | | | | |
|---|---|---|---|---|---|---|---|---|---|
| | G1 | G2 | L | N1 | S1 | S2 | U1 | U2 | Y |
| S. galilaeus ATCC 14969 | 42 | 68 | 55 | 126 | 63 | 145 | 115 | 63 | 43 |
| S. sp. ME 505-HE1 (FERM P-3667) ATCC 31273 | — | — | — | — | 143 | 89 | 97 | 101 | — |
| S. cinereoruber ATCC 19740 | 25 | 37 | 38 | 76 | 88 | 79 | 27 | 83 | 16 |
| S. niveoruber ATCC 14971 | — | 56 | — | 43 | 54 | 38 | — | 64 | 12 |
| S. antibioticus ATCC 8663 | — | 28 | — | — | — | 18 | — | 32 | — |
| S. purpurascens | — | 13 | — | — | — | 9 | — | 14 | — |

-continued

| Strains | MA 144 obtained (mg.) | | | | | | | | |
|---|---|---|---|---|---|---|---|---|---|
| | G1 | G2 | L | N1 | S1 | S2 | U1 | U2 | Y |
| ATCC 25489 | | | | | | | | | |

S. = *Streptomyces*

EXAMPLE 6

A mixture of the livers isolated from 5 male guinea pigs (500 g.) and 10 volumes of 10 mM Tris-HCl buffer (pH 7.8) containing 10 mM magnesium chloride and 0.25 M sucrose were homogenized by a Teflon homogenizer and centrifuged at 10,000 rpm for 20 min. The supernatant (400 ml.) obtained was mixed with 50 ml. of 4 mg./ml. aclacinomycin A and 50 ml. of 6 mg./ml NADP, distributed 50 ml. each in 500-ml. flasks, and incubated at 40° C. for 1 hr. on a rotary shaker. Reaction was terminated by the addition of two volumes of a cold chloroform-methanol (1:1) (v/v) mixture. This solution was mixed well and separated from the chloroform layer, and the remaining active fraction in the aqueous layer was re-extracted with an equal volume of chloroform. Both chloroform layers were combined, concentrated under reduced pressure, applied onto silicic acid thin-layer plates (Merck Co. 60F$_{254}$) and developed with a chloroform-methanol (10:1) (v/v) mixture for preparation. After chromatography, the band corresponding to MA 144-N1 was scratched off. MA 144-N1 was extracted with a chloroform-methanol (10:1) (v/v) mixture and concentrated under reduced pressure. There was obtained 62.3 mg. of the yellow powder of MA 144-N1.

EXAMPLE 7

One gram of aclacinomycin A was dissolved in 40 ml. of ethyl acetate, mixed with 40 ml. water containing 100 mg. of sodium borohydride, and shaken vigorously for 20 min. at room temperature in a separatory funnel. The reaction was allowed to stand and separate from the ethyl acetate layer, and the extract was washed with NaCl-saturated solution containing 10$^{-3}$M EDTA, washed twice with water, and then concentrated after dehydration with anhydrous sodium sulfate. After silicic acid column chromatography (3×20 cm. column) using a toluene-methanol (100:3) (v/v) mixture, active fractions containing MA 144-N1 and MA 144-M1 were pooled, concentrated, and added to n-hexane. MA 144-N1 (250 mg.) and MA 144-M1 (400 mg.) were obtained as yellow powders.

EXAMPLE 8

MA 144-M1 (400 mg.) obtained in Example 7 was dissolved in 100 ml. of 0.5% hydrochloric acid and hydrolyzed at 20° C. for 15 min. After neutralizing with diluted alkaline to pH 7.0, MA 144-S1 was extracted twice with 200 ml. of chloroform, and the chloroform layers were pooled and concentrated under reduced pressure. Active fractions containing MA 144-N1 which were obtained by silicic acid column chromatography (3×25 cm. column) using a methanol-toluene (5:100) (v/v) mixture were pooled, concentrated and added to n-hexane. There was obtained 237 mg. of yellow powder of MA 144-S1.

EXAMPLE 9

A nutrient medium having the following composition was prepared:

| | | |
|---|---|---|
| Soluble starch | 1 | % (W/v %) |
| "Esusan meat" (Trademark for soybean powder | 2 | % |
| Yeast extract | 0.3 | % |
| K$_2$HPO$_4$ | 0.1 | % |
| MgSO$_4$ . 7H$_2$O | 0.1 | % |
| MnCl$_2$ . 4H$_2$O | 0.0005 | % |
| FeSO$_4$ . 7H$_2$O | 0.0005 | % |
| pH | 7.7 | |

Fifty ml. of this medium was sterilized at 120° C. for 15 min. in a 500-ml. flask, inoculated with *Streptomyces galilaeus* MA 144-M1 (ATCC 31133) and incubated at 28° C. for 3 days on a rotary shaker.

The cultured broth obtained was centrifuged and adjusted to pH 7.2 with 1 N sodium hydroxide. To the supernatant was added ammonium sulfate up to 50% saturation. The reaction mixture was then allowed to stand overnight at 8° C. After centrifuging, the resulting precipitate was dissolved in 300 ml. of 0.01 M Tris-HCl buffer (pH 7.2), and dialyzed against 40 times volume of the above buffer overnight at 8° C. in the collodion bag. About 1000 units/ml. of crude enzyme preparation were obtained.

The enzyme reaction to produce MA 144-Y was carried out as follows: One gram of aclacinomycin A was dissolved in 20 ml. of methanol and 10 ml. of 0.05 N HCl and mixed with 200 ml. of 1 M citrate buffer (pH 5.5), 80 ml. of the above-prepared crude enzyme solution and 4000 ml. of distilled water. One hundred ml. of the reaction mixture were distributed into a 500-ml. flask and shaken for 5 hrs. at 28° C. on a rotary shaker. The reaction mixture was adjusted to pH 6.8 with 1 N sodium hydroxide, extracted with 1 l toluene, and concentrated to 30 ml. under reduced pressure. The precipitate obtained by the addition of 300 ml. n-hexane to the concentrate was 90% pure powder of MA 144-Y (0.95 g.). This crude powder of MA 144-Y was dissolved in 5 volumes of toluene, subjected to a silicic acid column (Wako gel C-200, 100 g.), and chromatographed with 1.7% methanol-containing toluene at 5° C. Active fractions obtained were concentrated to dryness, and 0.82 g. of pure MA 144-Y was obtained as a yellow powder.

EXAMPLE 10

Preparation of DNA Complexes

MA 144-Y (50 mg.) is dissolved in 0.01 N HCl and diluted up to 50 ml. with sterile 0.01 M phosphate buffer (pH 6.0) solution. Calf thymus DNA (500 mg.; highly polymerized, type 5, Sigma Co.) is dissolved in 50 ml. of the same buffer solution and autoclaved for 15 minutes at 120° C. followed by rapid cooling. The MA 144-Y solution is then mixed sterilely with the DNA solution and dialyzed against sterile saline water for 24 hours to form a solution of MA 144-Y DNA complex.

If the above procedure is repeated with the MA 144-Y used therein replaced by an equimolar weight of MA 144-G1, -G2, -L, -S1, -N1 and -U1, there are obtained the corresponding DNA complexes of the named anthracycline glycosides.

EXAMPLE 11

Salt Formation

Illustrative of the procedures which may be used to prepare acid addition salts, the tartaric acid salts of MA 144-G1, -G2, -L, -S1, -N1, -U1 and -Y may be prepared by separately dissolving 1 g. of the desired anthracycline and 100 g. tartaric acid in 500 ml. of ethyl acetate, mixing the solutions and concentrating in vacuo to dryness.

The hydrochloride salts may be prepared according to the following general procedure:

One hundred mg. of purified anthracycline is suspended in 50 ml. of distilled water and gradually dissolved by the addition of 0.1 N HCl. Addition of the HCl is stopped when the solution pH reaches 5.0. After passing through a Millipore filter PH (Millipore Co.), two ml. of the solution is transferred into a 15 ml. vial and freeze-dried.

We claim:

1. An anthracycline glycoside of the general formula

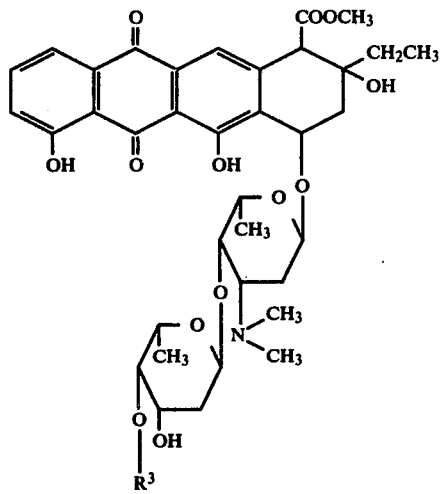

wherein $R^3$ is hydrogen,

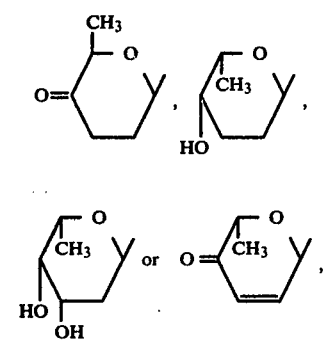

or a non-toxic acid addition salt thereof or a complex thereof with deoxyribonucleic acid.

2. The anthracycline glycoside MA 144-G1 of the formula

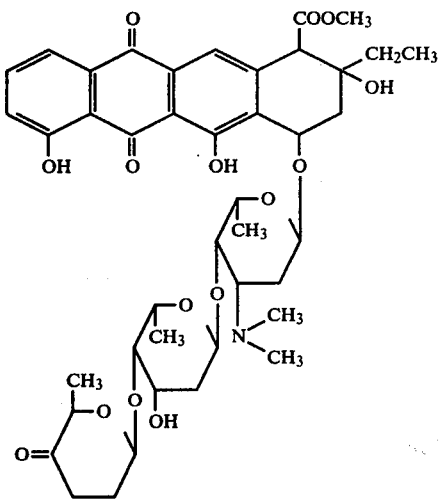

or a non-toxic acid addition salt thereof or a complex thereof with deoxyribonucleic acid.

3. The anthracycline glycoside MA 144-S1 of the formula

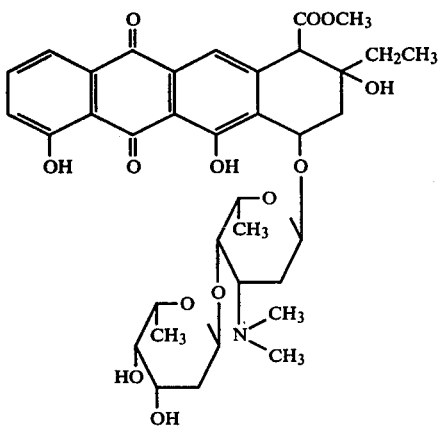

or a non-toxic acid addition salt thereof or a complex thereof with deoxyribonucleic acid.

4. The anthracycline glycoside MA 144-N1 of the formula

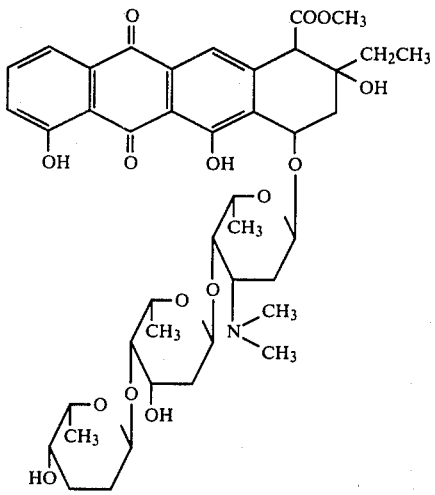

or a non-toxic acid addition salt thereof or a complex thereof with deoxyribonucleic acid.

5. The anthracycline glycoside MA 144-U1 of the formula

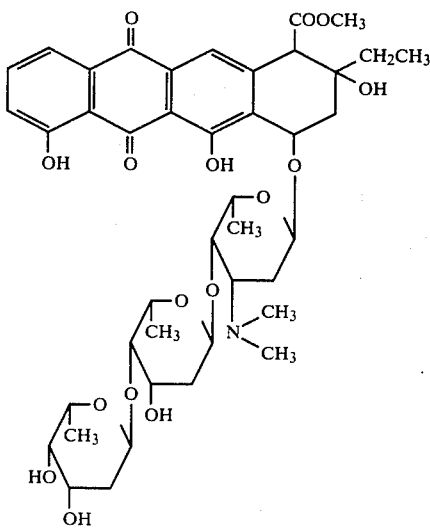

or a non-toxic acid addition salt thereof or a complex thereof with deoxyribonucleic acid.

6. The anthracycline glycoside MA 144-Y of the formula

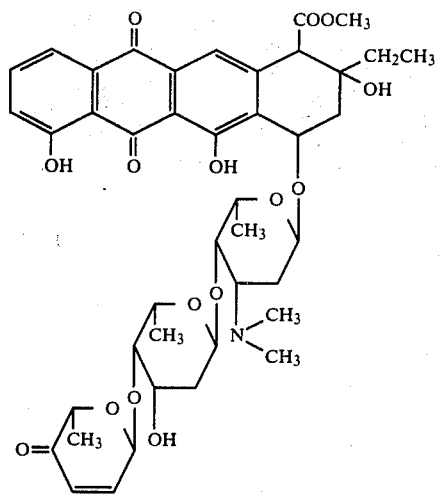

or a non-toxic acid addition salt thereof or a complex thereof with deoxyribonucleic acid.

7. The anthracycline glycoside MA 144-G2 of the formula

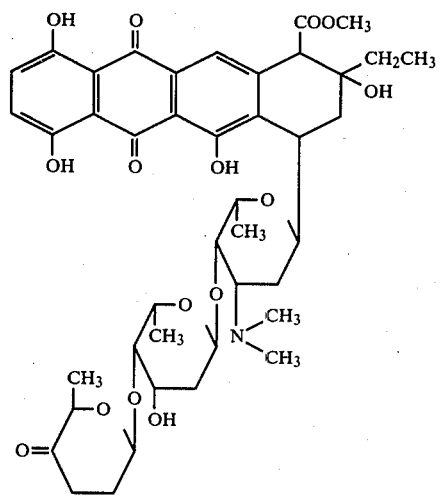

or a non-toxic acid addition salt thereof or a complex thereof with deoxyribonucleic acid.

8. The anthracycline glycoside MA 144-L of the formula

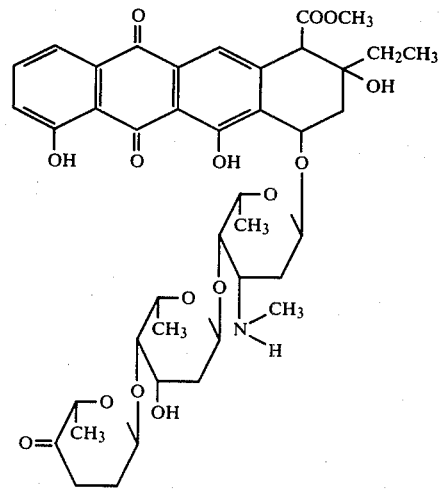

or a non-toxic acid addition salt thereof or a complex thereof with deoxyribonucleic acid.

9. A pharmaceutical composition comprising an effective antibacterial amount of MA 144-G1, -G2, -L, -S1, -N1, -U1 or Y, or a non-toxic acid addition salt thereof or a complex thereof with deoxyribonucleic acid, in combination with in inert pharmaceutically acceptable carrier of diluent.

* * * * *